United States Patent
Kwon et al.

(10) Patent No.: US 6,939,561 B2
(45) Date of Patent: Sep. 6, 2005

(54) METHODS AND COMPOSITIONS FOR POLYENE ANTIBIOTICS WITH REDUCED TOXICITY

(75) Inventors: Glen S. Kwon, Waunakee, WI (US); John Samuel, Edmonton (CA); Afsaneh Lavasanifar, Edmonton (CA)

(73) Assignee: Wisconsin Alumni Research Foundation, Madison, WI (US)

( * ) Notice: Subject to any disclaimer, the term of this patent is extended or adjusted under 35 U.S.C. 154(b) by 398 days.

(21) Appl. No.: 10/187,317

(22) Filed: Jun. 28, 2002

(65) Prior Publication Data

US 2003/0086964 A1 May 8, 2003

Related U.S. Application Data

(60) Provisional application No. 60/302,109, filed on Jun. 28, 2001.

(51) Int. Cl.[7] .............................. A61K 9/00; A61K 9/10; A61K 9/127; A61K 9/14; A61K 47/30
(52) U.S. Cl. ........................ 424/484; 424/400; 424/486; 424/488; 514/772.1
(58) Field of Search ................................. 424/400, 484, 424/486, 488; 514/772.1

(56) References Cited

U.S. PATENT DOCUMENTS

| | | | |
|---|---|---|---|
| 5,059,591 A | 10/1991 | Janoff et al. | .................... 514/31 |
| 5,449,513 A | 9/1995 | Yokoyama et al. | ....... 424/78.08 |
| 5,510,103 A | 4/1996 | Yokoyama et al. | ....... 424/78.08 |
| 5,686,110 A | 11/1997 | Greenwald et al. | .......... 424/486 |
| 5,885,613 A | 3/1999 | Holland et al. | |
| 5,925,720 A | 7/1999 | Kataoka et al. | .............. 525/523 |
| 5,929,177 A | 7/1999 | Kataoka et al. | .............. 525/408 |
| 2002/0082362 A1 * | 6/2002 | Brocchini et al. | ........... 525/461 |

FOREIGN PATENT DOCUMENTS

WO 85/05030 11/1985 ............ A61K/9/40

OTHER PUBLICATIONS

Allen, C et al. (1999), "Nano–Engineering Block Copolymer Aggregates for Drug Delivery;" *Colloids & Surfaces B: Biointerfaces* 16:3–27.

Brajtburg, J et al. (1996), "Carrier Effects on Biological Activity of Amphotericin B;" *Clin. Microbiol. Rev.* 9(4):512–531.

(Continued)

*Primary Examiner*—Thurman K. Page
*Assistant Examiner*—Simon J. Oh
(74) *Attorney, Agent, or Firm*—Greenlee, Winner & Sullivan, P.C.

(57) ABSTRACT

Provided are methods and compositions for reducing the toxicity of certain hydrophobic therapeutic agents, especially polyene antibiotics, in particular, Amphotericin B (AmB), and therapeutics such as paclitaxel, tamoxifen, an acylated prodrug or an acylated cis-platin, by incorporating these agents within micelles comprising an amphiphilic block-forming copolymer. Where the polyene is amphotericin B, desirably the spacer is an alkyl molecule of aabout 2 to about 8 carbon atoms, desirably 6 carbon atoms, and the core is an N-alkyl molecule of about 8 to about 28 carbon atoms, desirably 12 to 22 carbon atoms, advantageously, 12 to 18 carbon atoms, and as specifically embodied, 18 carbon atoms (stearate moiety). For the formulation of a larger polyene, the spacer and core are proportionately larger than those for amphotericin B. As specifically exemplified herein, the polymer backbone is a PEO of about 270 units with about 10-30 core-forming PLAA subunits, and advantageously about 14-24. Desirably the stearate moiety has a substitution level on the copolymer from about 35 percent to about 70 percent.

17 Claims, 13 Drawing Sheets

Espuelas, MS et al. (1998), "Interaction of Amphotericin B with Polymeric Colloids. A Spectroscopic Study;" *Colloids and Surfaces BN: Biointerfaces* 11:141–151.

Forster, D et al. (1988), "Toxicity of Solubilized and Colloidal Amphoterican B Formulations to Human Erythrocytes;" *Journal Pharm. Pharmacol.* 40:325–328.

Kataoka, K. et al. (Feb. 2000), "Doxorubicin–Loaded Poly(ethylene glycol)–Poly(β–benzyl–L–aspartate) Copolymer Micelles: Their Pharmaceutical Characteristics and Biological Significance;" *Journal of Controlled Release* 64:143–153.

Kataoka, K et al. (1993), "Block Copolymer Micelles as Vehicles for Drug Delivery;" *Journal of Controlled Release* 24:119–132.

Kwon, GS et al. (1999), "Soluble Self–Assembled Block Copolymers for Drug Delivery;" *Pharm. Res.* 16(5):597–600.

Kwon, GS (1998), "Diblock Copolymer Nanoparticles for Drug Delivery;" *Crit. Rev. Ther. Drug Carrier Syst.* 15(5):481–512.

Kwon, G et al. (1993), "Micelles Based on AB Block Copolymers of Poly(ethylene oxide) and Poly(β–benzyl L–aspartate);" *Langmuir* 9:945–949.

Kwon, GS et al. (1994), "Block Copolymer Micelles as Vehicles for Hydrophobic Drugs;" *Colloids & Surfaces B: Biointerfaces* 2:429–434.

Lavasanifar, A et al. (Apr. 2002), "Block Copolymer Micelles for the Encapsulation and Delivery of Amphotericin B;" *Pharm. Res.* 19(4):418–422.

Lavasanifar, A et al. (Feb. 2002), "The Effect of Fatty Acid Substitution on the In Vitro Release of Amphotericin B from Micelles Composed of Poly(ethylene oxide)–Blockpoly(N-hexyl stearate–L–aspartamide);" *Journal of Controlled Release* 79:165–172.

Lavasanifar, A et al. (Nov. 2001), "Micelles Self–Assembled from poly(ethylene oxide)–Block–poly(N–hexyl stearate–L–aspartamide) by a Solvent Evaporation Method: Effect on the Solubilization and Haemolytic Activity of Amphotericin B;" *Journal of Controlled Release* 77:155–160.

Lavasanifar, A et al. (Dec. 2000), "Micelles of poly(ethylene oxide)–block–poly(N–alkyl stearate L–aspartamide): Synthetic Analogues of Lipoproteins for Drug Delivery;" *Journal Biomed. Mater. Res.* 52:831–835.

Lavasanifar, A et al. (1999), "Artificial Lipoproteins for the Delivery of Amphotercin B;" *Proc. Int. Symp. Controlled Release Bioact. Mater.* 26:647–648.

Li, Y et al. (May 2000), "Methotrexate Esters of Poly(ethylene oxide)–Block–Poly(2–hydroxyethyl–L–aspartamide). Part I: Effects of the Level of Methotrexate Conjugation on the Stability of Micelles and on Drug Release;" *Pharm. Res.* 17(5):607–611.

Li, Y et al. (1999), "Micelle–like Structures of poly(ethylene oxide)–block–poly(2–hydroxyethyl aspartamide)–methotrexate Conjugates;" *Colloids & Surfaces B: Biointerfaces* 16:217–226.

Nagarajan, R et al. (1986), "Unusual Selectivity in Solubilization by Block Copolymer Micelles;" *Langmuir* 2:210–215.

Nakanishi, T et al. (Jul. 2001), "Development of the Polymer Micelle Carrier System for Doxorubicin;" *Journal of Controlled Release* 74:295–302.

Otsubo, T et al. (1998), "Long–Circulating Immunoliposomal Amphotericin B Against Invasive Pulmonary Aspergillosis in Mice;" *Antimicrobial Agents and Chemotherapy* 42(1):40–44.

Van Etten, EWM et al. (1998), "Superior Efficacy of Liposomal Amphotericin B with Prolonged Circulation in Blood in the Treatment of Severe Candidiasis in Leukopenic Mice;" *Antimicrobial Agents and Chemotherapy* 42(9):2431–2433.

Walsh, TJ et al. (1998), "Safety, Tolerance, and Pharmacokinetics of a Small Unilamellar Liposomal Formulation of Amphotericin B (AmBisome) in Neutropenic Patients;" *Antimicrobial Agents and Chemotherapy* 42(9)2391–2398.

Yokoyama, M et al. (1998), "Incorporation of Water–Insoluble Anticancer Drug into Polymeric Micelles and Control of Their Particle Size;" *Journal of Controlled Release* 55:219–229.

Yokoyama, M et al. (1998), "Characterization of Physical Entrapment and Chemical Conjugation of Adriamycin in Polymeric Micelles and Their Design for In Vivo Delivery to a Solid Tumor;" *Journal of Controlled Release* 50:79–92.

Yokoyama, M et al. (1992), "Preparation of Micelle–Forming Polymer–Drug Conjugates;" *Bioconjugate Chem.* 3:295–301.

Yu, BG et al. (1998), "In Vitro Dissociation of Antifungal Efficacy and Toxicity for Amphotericin B–Loaded Poly(Ethylene Oxide)–Block–Poly(β–benzyl–L–aspartate) Micelles;" *Journal of Controlled Release* 56:285–291.

Yu, BG et al. (1998), "Polymeric Micelles for Drug Delivery: Solubilization and Haemolytic of Amphotericin B," *Journal of Controlled Release* 53:131–136.

Lavasanifar, A. et al. (Oct. 2001) "The Effects of Alkyl Core Structure on Micellar Properties in Poly(ethylene oxide-block–Poly Aspartic Acid Derivatives;" Colloids & Surfaces B: *Biointerfaces* 22:115–126.

* cited by examiner $x = 270$
$y + z = 24$

FIG. 2

$$CH_3O(CH_2CH_2O)_x(CH_2)_3 S(CH_2) NH-(COCHNH)_y(COCHNH)_z H$$

with branches:
- first branch: $CH_2$ — $CH_3(CH_2)_nCO_2(CH_2)_mHNCO$
- second branch: $CH_2$ — $CONH(CH_2)_mOH$

| x | y + z | m | n |
|---|-------|---|----|
| 270 | 15 | 2 | 4 |
| 270 | 15 | 2 | 8 |
| 270 | 15 | 2 | 12 |
| 270 | 15 | 2 | 16 |
| 270 | 15 | 6 | 8 |
| 270 | 15 | 6 | 12 |
| 270 | 15 | 6 | 16 |
| 270 | 15 | 6 | 20 |
| 270 | 24 | 2 | 16 |
| 270 | 24 | 6 | 16 |

FIG. 5A
FIG. 5B
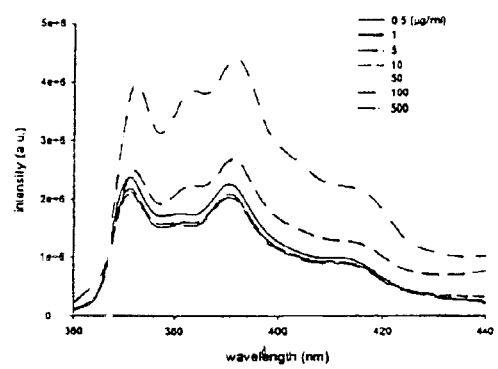
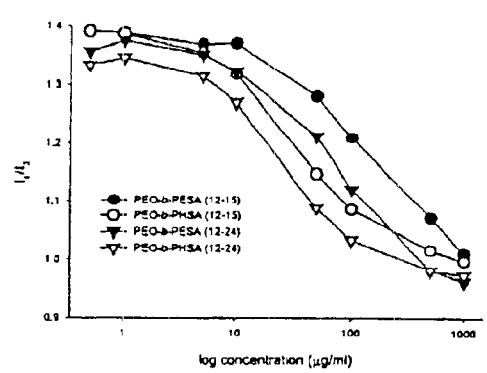

Wavelength (nm)

PEO-b-PHSA

| Stearic acid substitution level (%) | x | y | z |
|---|---|---|---|
| 11 | 270 | 3 | 21 |
| 50 | 270 | 12 | 12 |
| 70 | 270 | 17 | 7 |

AmB

100 # METHODS AND COMPOSITIONS FOR POLYENE ANTIBIOTICS WITH REDUCED TOXICITY

CROSS REFERENCE TO RELATED APPLICATIONS

This application claims benefit of U.S. Provisional Application No. 60/302,109, filed Jun. 28, 2001, which is incorporated herein by reference.

ACKNOWLEDGMENT OF FEDERAL RESEARCH SUPPORT

This invention was made, at least in part, with funding from the National Institutes of Health (NIH grant AI43346-01). Accordingly, the United States Government has certain rights in this invention.

BACKGROUND OF THE INVENTION

The field of the present invention is the area of methods of formulating pharmaceutical compositions for medical and/or veterinary use, in particular, methods of formulating relatively insoluble or toxic materials such as polyene antibiotics, e.g., amphotericin B and nystatin, so that solubility in aqueous milieus is improved and so that toxicity is reduced, release is controlled and in at least some instances, the stability of the formulation is improved. Similarly, solubility is increased and toxicity is decreased for such cancer therapeutic agents as paclitaxel and tamoxifen.

Fungal infections are, in part, associated with immune-compromised patients such as those infected with HIV, patients who have been subjected to anticancer therapeutics or immune suppressive drugs after organ transplants, and the elderly. Fungal infections fall into two categories: systemic (deep) mycoses and superficial mycoses which involve the skin or mucous membranes. The dermatophytic fungi infect the skin, hair and nails; etiological agents include *Epidermiphyton* spp., *Trichophyton* spp. and *Microspermum* spp. Generally, infections of the mucous membranes are due to infections with *Candida albicans*. The systemic mycoses are serious and often life-threatening. They include cryptococcosis, systemic candidiasis, aspergillosis, blastomycosis, histoplasmosis, coccidiodomycosis, paracoccidioidomycosis, phycomycosis, torulopsosis, among others.

The three families of drugs used to treat fungal infections are the polyenes, imidazoles and antimetabolites. The polyenes include nystatin, which is generally used for superficial infections only, and amphotericin B. Mepartricin and natrimycin are other polyenes with antifungal activities.

Ketoconazole, miconazole and thiabendazole are imidazoles with antifungal activity. They act by inhibiting cytochrome activity and by interfering with ergosterol synthesis. Flucytosine is an antimetabolite which has been used in the treatment of systemic mycoses. It is converted in vivo to 5-fluorouracil, which inhibits thymidylate synthetase.

Amphotericin B (AmB) has an affinity for membranes with a relatively high ergosterol content; it forms channels which allow the passage of potassium and other small molecules. Because the AmB is very toxic, especially in aggregates, and has numerous side effects, it must be given in a hospital setting, adding to treatment costs. There is some evidence (Beringue et al. (1999) *J. Gen. Virol.* 80, 1873–1877; Beringue et al. (2000) *J. Virol* 74, 5432–5440) that certain polyenes may inhibit the progression of scrapie infections.

Despite its low solubility in water and the toxicity problems, AmB is one of the drugs of choice for treating fungal infections. Notably, the development of resistance to AmB is very rare. Numerous strategies have been employed to improve its solubility in aqueous systems and to reduce its toxicity. Strategies for the improvement of solubility and toxicity have included formulation with surfactant, e.g. deoxycholate, liposome encapsulation, encapsulation in polyethylene glycol-complexed liposomes and encapsulation with various amphiphilic polymeric materials.

Amphiphilic PEO-block-poly(L-amino acid) (PEO-b-PLAA) polymers may form micelle structures that effectively encapsulate water-insoluble drugs (G. S. Kwon et al. (1994) *Colloids & Surfaces B: Biointerfaces* 2, 429–434; K. Kataoka et al. (2000) *J. Control. Release* 64, 143–153; M. Yokoyama et al. (1998) *J. Control. Release* 55, 219–229). PEO-b-PLAA micelles are unique among drug carrier systems, owing to nanoscopic dimensions, shell of PEO, and nonpolar core of PLAA, which can take up and "protect" water-insoluble drugs. A primary advantage of PEO-b-PLAA is the potential for encapsulation of drugs by chemical or physical means inside the core of the micelles, consisting of PLAA blocks (M. Yokoyama et al. (1992) *Bioconjugate Chem.* 3, 295–301; Y. Li and G. S. Kwon (1999) *Colloids & Surfaces B: Biointerfaces* 16, 217–226; A. Lavasanifar et al. (2000) *J. Biomed. Mater. Res.* 52 831–835). In either situation, it is possible to tailor the structure of a core-forming PLAA block in order to enhance properties of PEO-b-PLAA micelles for drug delivery (Y. Li, and G. S. Kwon (2000) *Pharm. Res.* 17(5), 607–611).

Because fungal infections are relatively difficult to treat, because systemic fungal inventions are often life-threatening, and because the antifungal antibiotics are often toxic to animals, including humans, there is a longfelt need in the art for pharmaceutical compositions comprising polyene antibiotics which are improved in relative toxicity to the patient and in release properties. Similarly, there is a need in the art for formulations of certain other pharmaceuticals, including but not limited to taxol, tamoxifen and other anticancer agents.

SUMMARY OF THE INVENTION

The present invention provides methods for formulating hydrophobic therapeutic agents such as polyene antibiotics, especially amphotericin B, such that toxicity is reduced. In particular, the polyene antibiotic is incorporated within micellar structures of block polymers comprising a hydrophilic backbone component, a spacer and a hydrophobic core. The hydrophilic backbone can be a polysaccharide, a polyethylene oxide polymer, among others, provided that it is nontoxic and suitable for parenteral administration in humans and animals and contains reactive functional groups which allow the attachment of spacer and hydrophobic core moieties. A number of suitable shell forming polymers and core forming backbones are described in U.S. Pat. No. 5,449,513. The spacer can be an alkyl, alkenyl or alkynyl moiety having from about 3 to about 10 carbon atoms, desirably 6. The hydrophobic core can be an alkyl moiety, an aryl moiety or other moiety, depending on the nature of the molecule to be encapsulated. Desirably, the molecule sizes and polarities of the spacer and core are proportioned according to the molecular dimensions and polarity properties of the polyene or other molecule (such as paclitaxel (taxol), tamoxifen or derivative) to be incorporated. Where the polyene is amphotericin B, desirably the spacer is an aliphatic molecule of about 6 carbon atoms and the core is an N-alkyl molecule of about 8 to about 28 carbon atoms, desirably 12 to 22 carbon atoms, advantageously, 12 to 18 carbon atoms, and as specifically embodied, 18 carbon atoms (stearate moiety). With reference to the structure of FIG. 1, x is from about 200 to about 400, n is from about 2 to about 8, and y+z is from about 10 to about 30. For the formulation of a larger polyene, the spacer and core are proportionately larger than those for amphotericin B. As specifically exemplified herein, the polymer backbone is a PEO of about 270 units with about 12–25 core-forming PLAA subunits, and advantageously about 22–24. See FIG. 1 for the structure.

The present invention further encompasses micelles formed by the solvent evaporation method which encapsulate AmB, other polyene or other therapeutic compounds such as taxol. Also within the scope of the present invention are freeze-dried preparations of the micelles of the present invention, as set forth above, especially those comprising a polyene such as AmB encapsulated with a PEO-b-PHSA material, especially with a block length of about 12–25. Also within the scope of the present invention are reconstituted micelles of the present invention, especially AmB-loaded micelles reconstituted in 5% sterile dextrose solution.

Where the molecule to be incorporated into the micelles is an aromatic compound, desirably the core also contains aromatic (aryl) moieties, for improved interactions between the compound to be incorporated and the amphiphilic molecule with which it is complexed for micelle formation. As specifically exemplified, the therapeutic agent-loaded micelles embodied in the present invention are formed by solvent evaporation of the solution of the therapeutic agent and the micell-forming agent, e.g., AmB and Poly(ethylene oxide)-block-poly(N-hexyl stearate L-aspartamide). The solvent evaporation technique provides surprisingly improved results with respect to toxicity and release rate as compared with prior art compositions.

BRIEF DESCRIPTION OF THE DRAWINGS

FIG. 2 illustrates chemical structure of fatty acid conjugates of PEO-b-PHAA. X can be from 100 to 300, y+z can be from 10 to 30, n can be from 0 to 8, and m can be from 8 to 20. The table below shows particular polymers which have been tested.

FIG. 3A: effect of spacer group and level of fatty acid conjugation in capric acid conjugates of PEO-b-PHAA. FIG. 3B: effect of PHAA block length in stearic acid conjugates of PEO-b-PHAA.

FIG. 5A provides the fluorescence emission spectra of pyrene in the presence of different concentrations of PEO-b-PHCA (12–15), and FIG. 5B illustrates the intensity ratio ($I_1/I_3$) of pyrene ($6 \times 10^{-7}$ M) from emission spectrum as a function of PEO-b-PHCA concentration. The plot is the average of three repeats of this experiment.

DETAILED DESCRIPTION OF THE INVENTION

Abbreviations used in the present disclosure include the following: PEO-b-PLAA, Poly(ethylene oxide)-block-poly(L-aspartic acid); PEO-b-PHSA, Poly(ethylene oxide)-block-poly(N-hexyl stearate L-aspartamide); PEO-b-PBLA, Poly(ethylene oxide)-block-poly(β-benzyl-L-aspartate); PEO-b-PHCA, Poly(ethylene oxide)-block-poly(N-hexyl caprate L-aspartamide)PEO-b-PHHA, Poly(ethylene oxide)-block-poly(hydroxyhexyl L-aspartamide); AmB, Amphotericin B; DMSO, N,N-dimethylsulfoxide; DMF, N,N-dimethylformamide; SEC, Size exclusion chromatography; RBC, red blood cell; PBS, phosphate buffered saline; MIC, minimum inhibitory concentration; colony forming units, CFU, colony forming units.

Figure 9:
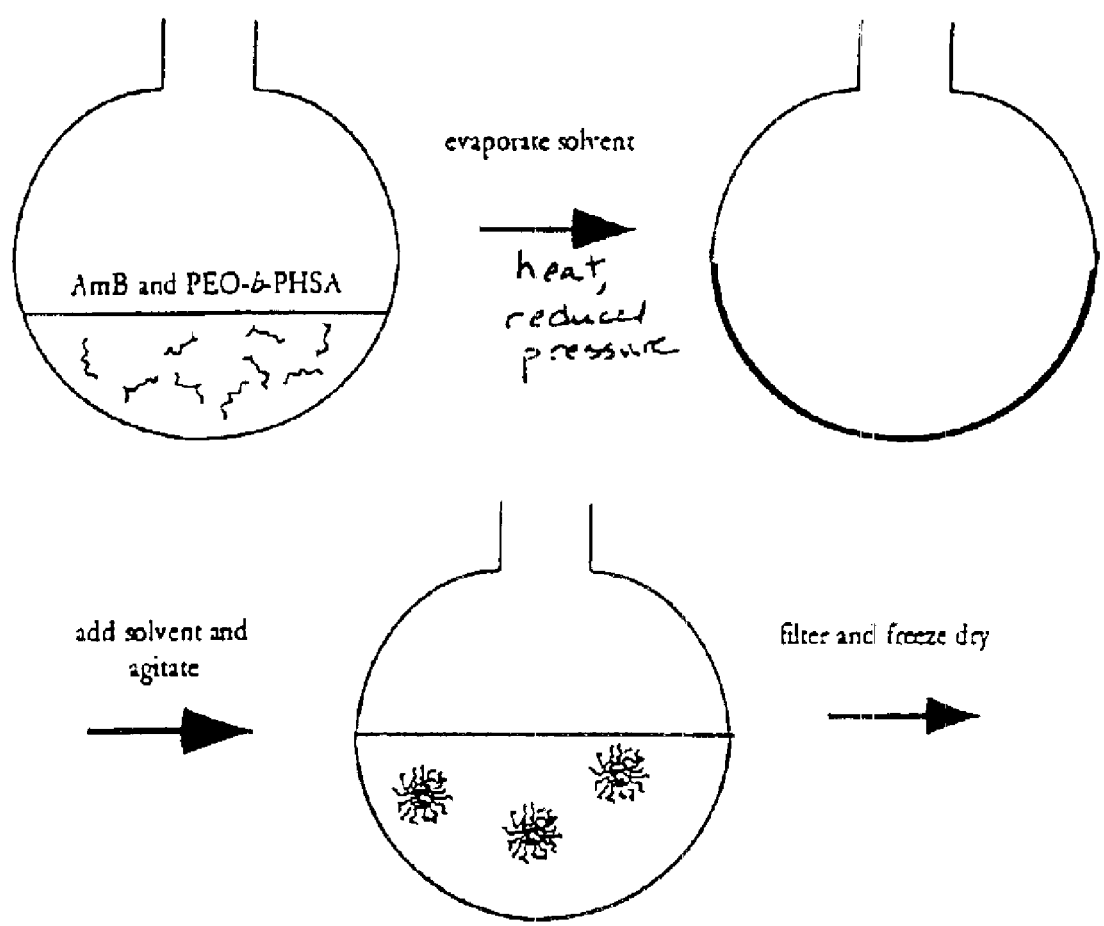
FIG. 9 schematically illustrates the solvent evaporation method of drug loading in PEO-b-PHSA micelles.

The solvent evaporation method used to encapsulate AmB in PEO-b-PHSA micelles is shown in FIG. 9. AmB and PEO-b-PHSA were dissolved in methanol, and a thin film of polymer and drug was coated on a round bottom flask by evaporation of methanol under vacuum with heat. Distilled water was added to dissolve the film and form PEO-b-PHSA micelles with encapsulated AmB, and the micellar solution was filtered (0.22 μm) and freeze-dried. The level of AmB in these solvent-evaporated PEO-b-PHSA micelles was 0.35 mol drug/mol polymer, and the yield of AmB encapsulation was 73% (Table 1). In contrast, the dialysis method provided 0.25 mol AmB/mol PEO-b-PHSA, and the yield of AmB encapsulation was 60%. In both cases, a higher initial level of drug resulted in higher drug content, but with an increase in hemolysis (data not shown). The reconstitution of freeze-dried samples yielded aqueous solutions having AmB levels greater than 250 μg/ml. For comparison, the solubility of AmB in water is about 0.5 to 1 μg/ml, and it is administered intravenously in its standard formulation, which contains sodium deoxycholate at 100 μg/ml.

Figure 1:
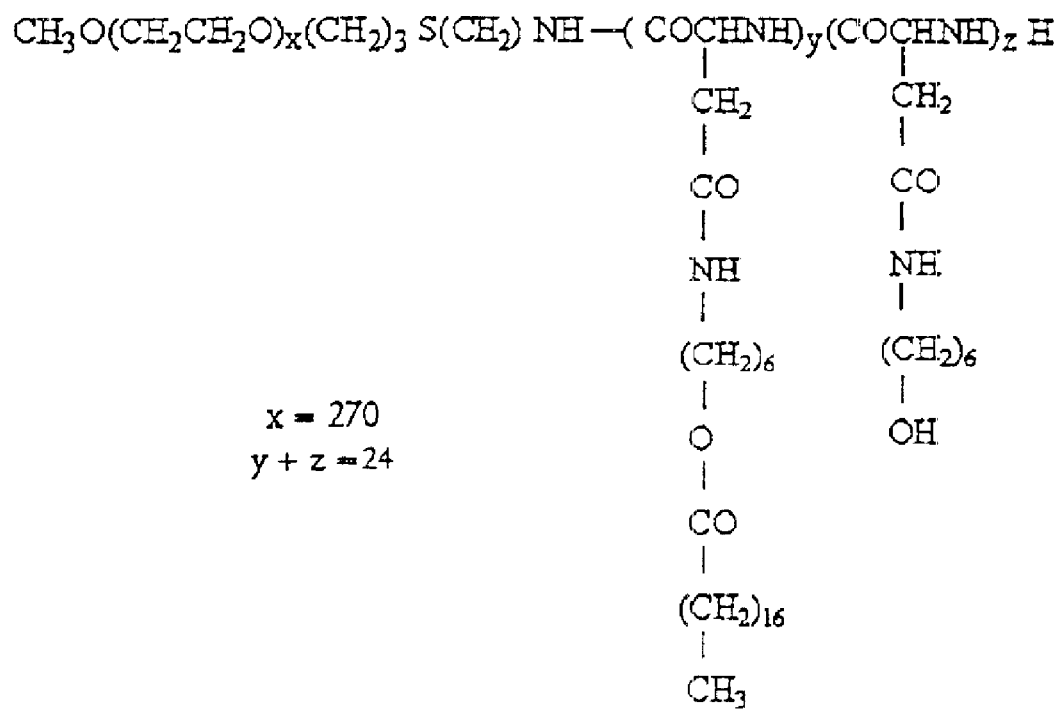
FIG. 1 presents the chemical structure of a specifically exemplified PEO-b-PHSA block copolymer and molecular model of this polymer.
Figure 1:
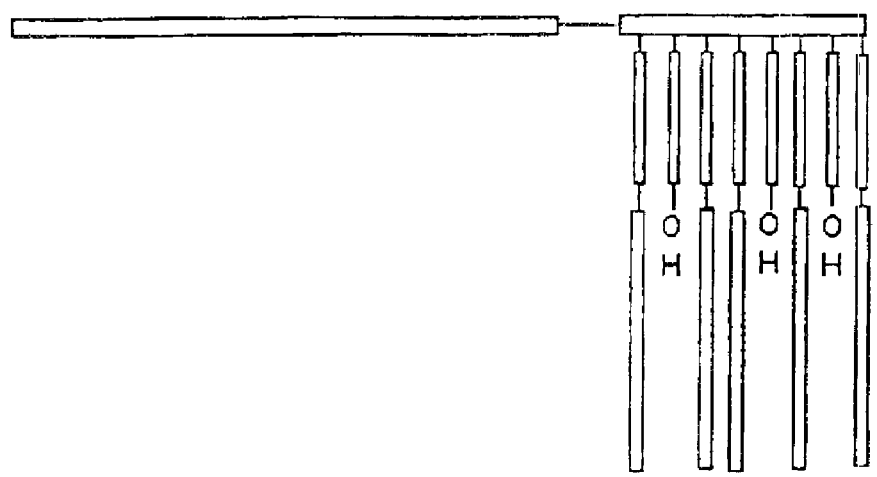
Figure 3A:
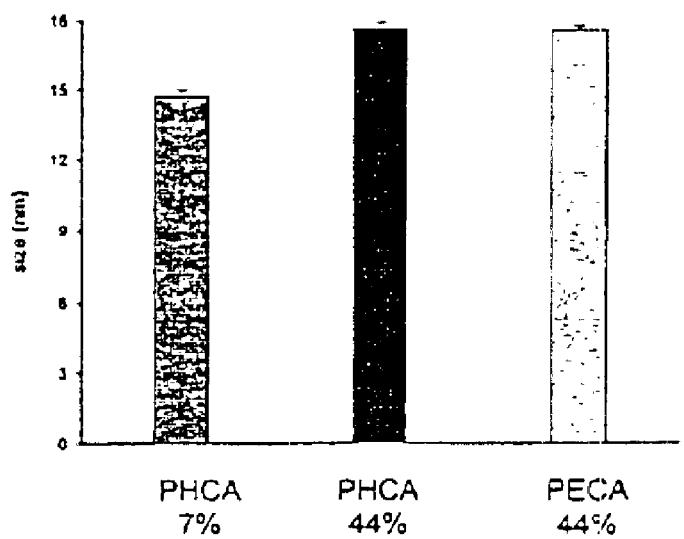
FIGS. 3A–3B show the effect of alkyl core structure on micellar size (mean±SE).

TEM provided evidence for the formation of spherical micelles made of PEO-b-PHSA when the solvent evaporation method was used for micelle formation and drug loading (FIG. 3A). The average diameter of PEO-b-PHSA micelles was 15.2±4.0 nm before freeze-drying. An increase in the micellar size to 22.3±4.7 nm was observed for the reconstituted samples (data not shown). PEO-b-PHSA micelles prepared by the dialysis method were also spherical (FIG. 3B), but significantly larger (average diameter of 25.0±4.9 nm) than PEO-b-PHSA micelles prepared by the solvent evaporation (P<0.0001, unpaired t test).

SEC provided evidence for the encapsulation of AmB in PEO-b-PHSA micelles. Aqueous solutions of AmB at concentrations of 1, 10 and 100 $\mu$g/ml eluted from the SEC column at 17.4, 17.3 and 16.5 min, respectively. In contrast, AmB encapsulated in PEO-b-PHSA micelles formed by dialysis and solvent evaporation methods eluted at 10.6±0.1 and 10.8±0.1 min, respectively, corresponding to a molecular weight of 2.9±106 and 2.4±10$^6$ g mol$^{-1}$ based on dextran standards. This also indicates that larger PEO-b-PHSA micelles are produced by the dialysis method (unpaired t test, P<0.05), consistent with TEM images (Table 1). The encapsulation of AmB in PEO-b-PHSA micelles at 0.25–0.35 mol drug:mol polymer caused no significant change in the elution time of PEO-b-PHSA micelles (unpaired t test, P>0.05). There was no evidence of unencapsulated AmB, which elutes at about 17.4 min in the chromatography system used in the experiments described herein.

Figure 7:
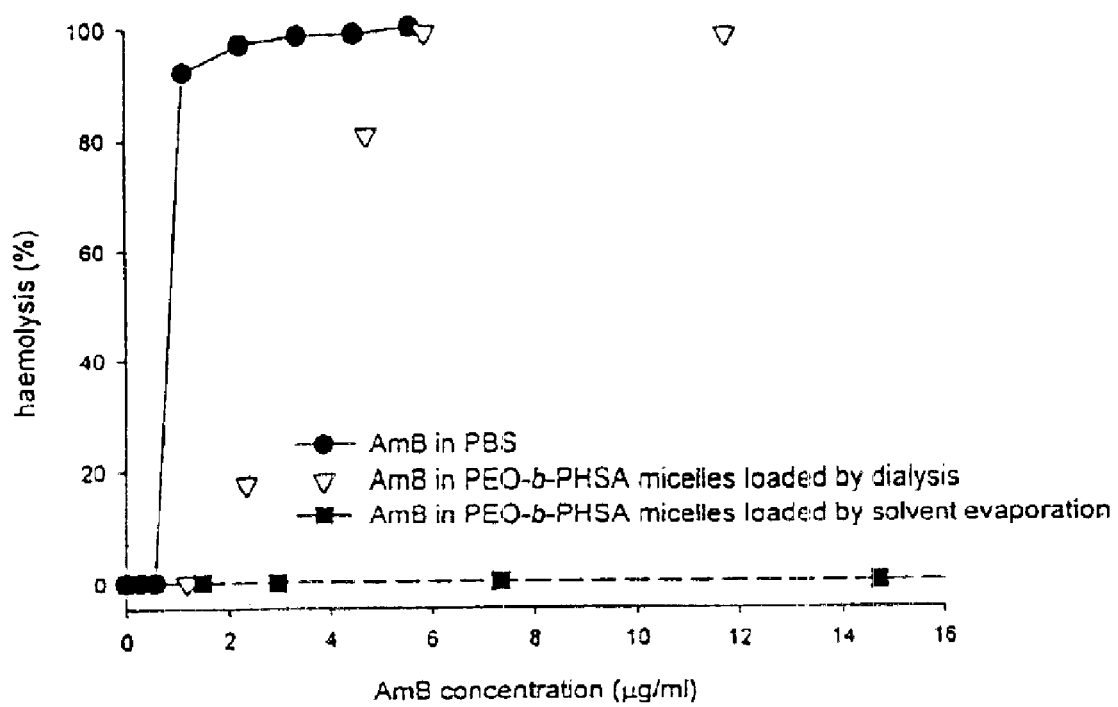
FIG. 7 shows the hemolytic action of AmB toward human red blood cells and the effect of the drug loading method on hemolysis.

The primary advantage of the solvent evaporation method was a reduction in hemolysis caused by AmB (FIG. 7). AmB itself caused 100% hemolysis at about 1 $\mu$g/ml. After encapsulation of AmB in PEO-b-PHSA micelles by the dialysis method, the drug was somewhat less toxic than AmB itself, causing 50% hemolysis at 3.8 $\mu$g/ml and 100% hemolysis at 6 $\mu$g/ml. In contrast, AmB encapsulated by the solvent evaporation method in PEO-b-PHSA micelles (polymer block length 22–25) was completely nonhemolytic at 22 $\mu$g/ml.

The results contrast with earlier findings with Pluronics, PEO-b-poly(propylene oxide)-b-PEO, which solubilizes AmB after encapsulation by a solvent evaporation method, but fails to protect RBCs from hemolysis (D. Forster et al. (1988) *J. Pharm. Pharmacol.* 40, 325–328). Without wishing to be bound by any particular theory, PEO-b-PHSA micelles are believed to reduce hemolysis by slowly releasing AmB over the 30 min time period of incubation of drug with RBCs or by the release of AmB in an unaggregated state, unimers, which are known to be non-toxic for mammalian cells (J. Brajtburg, and J. Bolard (1996) *Clin. Microbiol. Rev.* 9 512–531). Regardless, AmB encapsulated in PEO-b-PHSA micelles by the solvent evaporation method appears to be much less toxic in vitro than the standard formulation of AmB, and a similar reduction in toxicity in vivo is achieved.

The effects of spacer chain length and hydrophobic core fatty acid chain length were studied to determine optimum combinations on the PEO-b-PLAA backbone for the encapsulation of AmB. The preparation of various fatty acid esters of PEO-b-PHAA from PEO-b-PBLA with either 15 or 24 degrees of polymerization in the PBLA block was accomplished in two steps. In the first step, 2-HP was used as a catalyst to remove the benzyloxy group of PEO-b-PBLA and replace it with either 2-aminoethanol or 6-aminohexanol. As a result, poly(ethylene oxide)-block-poly(hydroxyethyl L-aspartamide)(PEO-b-PHEA) and poly(ethylene oxide)-block-poly(hydroxyhexyl L-aspartamide)(PEO-b-PHHA) were formed, respectively. PEO-b-PHEA and PEO-b-PHHA were then reacted with saturated fatty acids of various chain lengths ranging from 6 to 22 carbons in the presence of DCC and DMAP as coupling agent and catalyst, respectively. The general structure of the final product is shown in FIG. 2. Thin layer chromatography using diethyl ether: dichloromethane (20:80) as the mobile phase and 0.1% solution of bromocresol in ethanol as an indicator confirmed the purity of block copolymers from free fatty acids.

$^1$H NMR was used to estimate the level of fatty acid substitution on PEO-b-PHAA. Because the molecular weight of the PEO block was known and the purity of the synthesized copolymers was confirmed by TLC, comparison of characteristic peak intensities of fatty acid substituents (CH3, $\delta$=0.8 ppm) to that of PEO (—CH2-CH2-O—, $\delta$=3.6 ppm) provides an estimation of the degree of fatty acid attachment. The substitution of fatty acid is expressed as the percentage of conjugated stearic acid to hydroxyl groups of PEO-b-PHAA throughout the present application. Statistical analysis (ANOVA, Duncan's test) of the data obtained for different batches of synthesized polymers (with varied fatty acid chain lengths) reveals that the use of longer spacer groups significantly (P<0.01) increases the level of fatty acid substitution on the PHAA block.

Micellization of the fatty acid conjugates of PEO-b-PHAA having different core structures was achieved using a dialysis method, and the formation of micelle like structures was investigated by TEM. The TEM images clearly indicate the presence of spherical particles with nanoscopic dimensions. However, a tendency towards the formation of ellipsoids is seen when longer fatty acids (myristic and stearic) attached to $C_6$ spacer group with higher degrees of substitution (ca. 65%) were used.

Figure 3B:
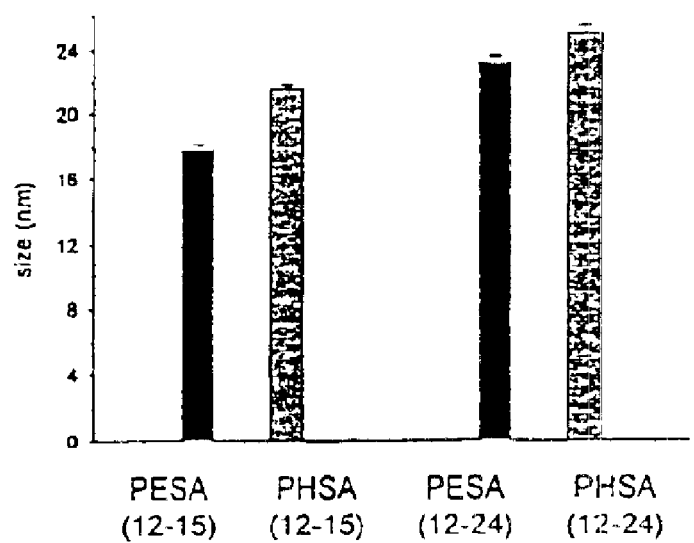

The average diameter of the prepared micelles measured from TEM images for 12–15 samples was found to be between 14.7–21.8 nm (Table 1). Increasing the substitution level of fatty acid on the polymeric backbone caused a significant increase (P<0.001) in micellar size as s shown for poly(ethylene oxide)-block-poly[N-(6-hexyl caprate)-L-aspartamide](PEO-b-PHCA) in FIG. 3A (7% vs 44%). The length of the spacer group showed no significant effect when micellar size was compared in capric acid conjugates of PEO-b-PHEA and in hexyl conjugates of PEO-b-PHHA with the same degree of fatty acid attachment (FIG. 3A). Increasing the length of the fatty acid chain caused a significant increase in micellar size (P<0.001) when polymer batches with similar degree of fatty acid attachment were compared (Table 1). The average diameter of stearic acid conjugates of PEO-b-PHEA and PEO-b-PHHA for 12–24 samples was measured to be between 23.3 to 25.3 nm. An increase in the length of the PLAA block from 15 to 24 also showed an enhancing influence (un paired t test, P<0.001) on micellar size when block copolymers with the same degree of stearic acid substitution on the PHEA or PHHA blocks were compared (FIG. 3B). The substitution level of stearic acid on the PHEA and PHHA block was calculated to be 45 and 60%, respectively in both PEO block length 12–15 and 12–24 samples.

Figure 4A:
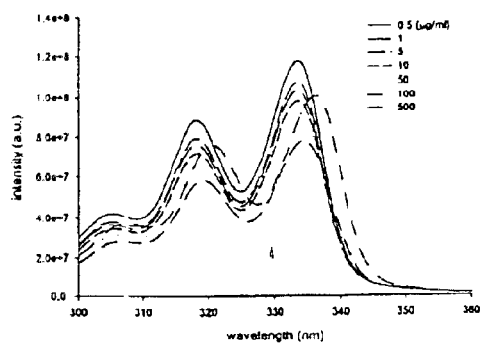
FIG. 4A provides fluorescence excitation spectra of pyrene in the presence of different concentrations of PEO-b-PHCA (12–15).
Figure 4B:
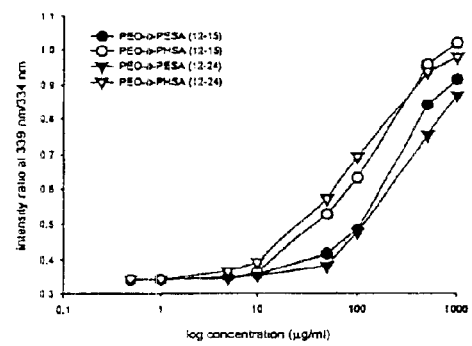
FIG. 4B illustrates intensity ratio (339 nm/334 nm) of pyrene ($6 \times 10^{-7}$ M) from excitation spectrum as a function of PEO-b-PHCA concentration. The plot is the average of three repeats of this experiment.

Pyrene was used as a fluorescent probe to determine the CMCs and the micropolarities of the core for micelles formed from fatty acid esters of PEO-b-PHAA. Following partitioning of pyrene into the micellar core at polymer levels above CMC, a red shift is seen in the excitation spectrum of pyrene (FIG. 4A). Therefore, the ratios of peak intensities at 339 nm over 334 nm are plotted vs. the logarithm of polymer concentration to determine CMC (FIG. 4B). The CMC is measured from a sharp rise in the intensity ratios at the onset of micellization (R. Nagarajan et al. (1986) *Langmuir* 2, 210; J. Georges (1990) *Spectrochimica Acta Reviewes* 13, 27; M. Winnik, S. T. A.

Figure 4C:
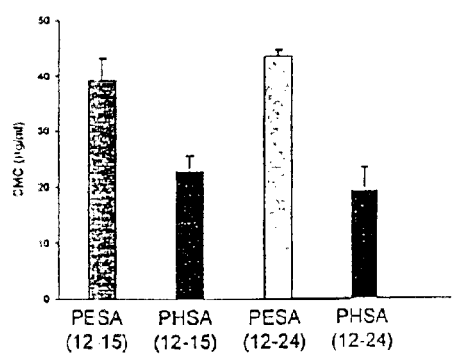
FIG. 4C shows the effect of PHAA block length in stearic acid conjugates of PEO-b-PHAA on CMC (mean±SE).
Figure 4D:
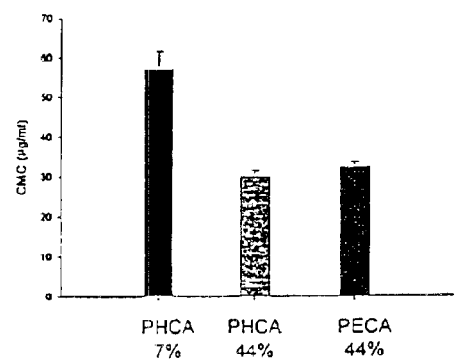
FIG. 4D shows the effect of spacer group and level of fatty acid conjugation in capric acid conjugates of PEO-b-PHAA on CMC (mean±SE).

Regismond, *Colloids & Surfaces A: Physicochemical & Engineering Aspects* 118 (1996) 1; G. S. Kwon et al. (1993) *Langmuir* 9, 945). The average CMCs for the polymeric micelles under study ranged from 9 to 50 μg/mL. Elongation of the fatty acid did not significantly affect CMC values obtained from this method of measurement (Table 1). As it is shown in FIGS. 4C and 4D, no significant effect (P>0.05) on CMC was observed when block copolymers with longer PHAA block or spacer group but similar level of fatty acid substitution were used, respectively. The substitution level of fatty acid on the PHAA block seems to be the major factor controlling the onset of micellization. As it is illustrated in FIG. 4D, a decrease in the level of capric acid attachment from 44 to 7% results in a reduced tendency for self-association in PEO-b-PHCA. The mean CMC value rose from 29 to 57 μg/ml in PEO-b-PHCA with 7% capric acid substitution.

The fluorescence emission spectrum of pyrene was also affected by the polarity of its environment (FIG. 5A). A sharp decrease in the relative intensity of the first ($I_1$) to the third band ($I_3$) was observed at the CMC as pyrene partitions to the non-polar core of the micelles (FIG. 5B). The $I_1/I_3$ ratios obtained from emission spectra of pyrene in the presence of 500 μg/mL of fatty acid ester of PEO-b-PHAA (12–15) are reported in Table 1. A ratio of 1.4 was observed for aqueous pyrene, which is in agreement with previous observations (J. Georges (1990) *Spectrochimica Acta Rev.* 13, 27). At low polymer concentrations, the ratio was close to what has been found for water. As the concentration of the polymer increased, the $I_1/I_3$ ratio dropped to about 1.0. The reduced value of $I_1/I_3$ ratio indicates non-polar micro-domains in micelles, with polarities similar to n-pentanol in the pyrene scale (Dong et al. (1984) *Can. J. Chem.* 62, 2560). No significant effect on $I_1/I_3$ was detected when different structural factors were altered in fatty acid conjugates of PEO-b-PHAA, P>0.05 (Table 1, FIG. 5B).

Figure 6A:
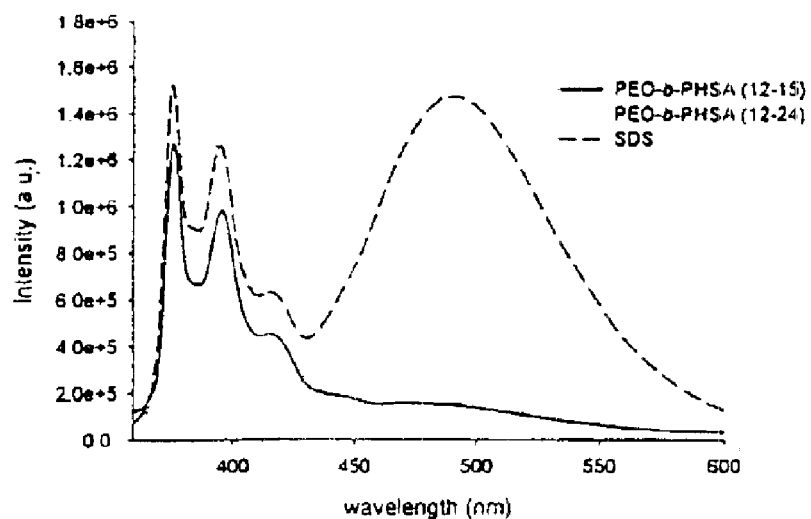
FIG. 6A depicts the fluorescence emission spectrum of 1,3-(1,1'-dipyrenyl)propane in micellar solutions of PEO-b-PHSA in comparison to SDS.
Figure 6B:
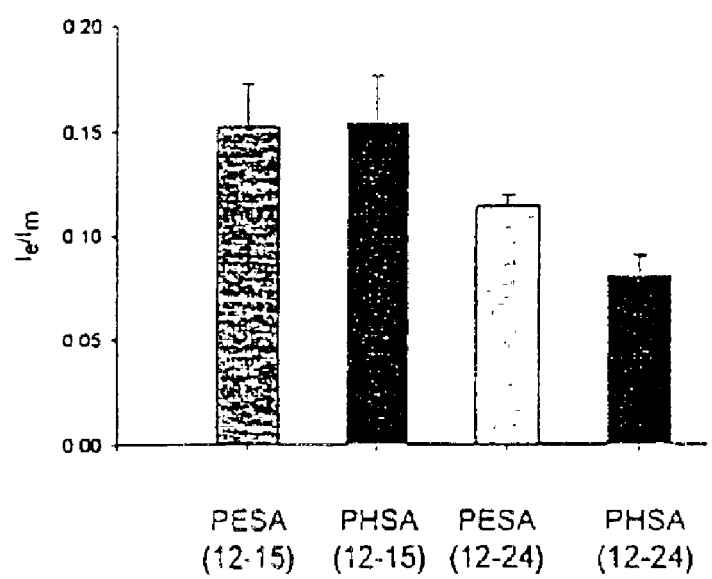
FIG. 6B shows the effect of PHAA block length on microviscosity in stearic acid conjugates of PEO-b-PHAA.

Evidence for the limited motion of fatty acid esters in the micellar core was obtained from the fluorescence emission spectrum of 1,3-(1,1'-dipyrenyl)propane in the presence of 500 μg/mL of polymeric micelles (FIG. 6A). Like pyrene, 1,3-(1,1'-dipyrenyl)propane is a hydrophobic fluorescent probe that preferentially partitions into the hydrophobic micro-domains of micelles at polymer concentrations above the CMC. By changing its conformation, 1,3-(1,1'-dipyrenyl)propane forms intramolecular pyrene excimers that emit light at 480 nm when excited at 390 nm. The conformational change in 1,3-(1,1'-dipyrenyl)propane probe is restricted by a local friction imposed by the viscosity of its environment. Therefore, the ratio of the intensity of the light emitted from excited dipyrene excimer ($I_e$) to that of isolated pyrene monomer ($I_m$) in its emission spectrum is used as a measure of effective viscosity (Georges (1990 supra). As shown in Table 1 and FIG. 6, $I_e/I_m$ ratios are very low for all the copolymers under study, reflecting rigid structures for the polymeric micellar cores. In contrast, a high incidence of excimer formation in sodium lauryl sulfate (SDS) reflects the liquid like core of a low molecular weight surfactant (FIG. 6A). No significant change (P>0.05) in $I_e/I_m$ ratios was detected for different fatty acids attached to the polymeric backbone in 12–15 samples (Table 1). However, behenic acid conjugates of PEO-b-PHHA with substitution levels of 65% showed lowered $I_e/I_m$ ratio (0.08) in comparison to other copolymers (Table 1). Beside this specific structure, lower average $I_e/I_m$ ratios in 12–24 samples of poly(ethylene oxide)-block-poly[N-(2-ethyl stearate)-L-aspartamide] (PEO-b-PESA) poly(ethylene oxide)-block-poly[N-(6-hexyl stearate)-L-aspartamide] (PEO-b-PHSA) compared to 12–15 species indicates the elongation of the PHAA block causes more restricted motions in the micellar core environment as well (FIG. 6B).

It is known that amphiphilic block copolymers can form supramolecular core/shell structures in aqueous environment through the expulsion of their hydrophobic segments from water and further hydrophobic association of these blocks. Supramolecular self-assembled structure plays an analogous role to natural carriers with several advantages such as ease of chemical modification, stability and safety (Kwon et al. (1999) *Pharm. Res.* 16, 597; G. S. Kwon (1998) *Crit. Rev. Ther. Drug Carrier Syst.* 15, 481). To achieve optimized micellar properties and drug loading capacities we pursued the chemical tailoring of the core structure in PEO-b-PLAA in our recent research studies. Compatibility between the solubilizate and the core-forming block is proven to be necessary for efficient solubilization of water insoluble molecules in micellar systems (Allen et al. (1999) *Colloids & Surfaces B: Biointerfaces* 16, 3; Yokoyama et al. (1998) *J. Control. Release* 55, 219; Nagarajan et al. (1986) *Langmuir* 2, 210; Yokoyama et al. (1998) *J. Control Release* 50, 79). With this in mind, the chemical structure of the core-forming block in PEO-b-PLAA was tailored to aliphatic ones to enhance the solubilization of compatible drugs such as the polyene antibiotics, especially AmB.

Chemical modification of the core structure in PEO-b-PLAA block copolymers was carried out through replacement of benzyloxy group in PEO-b-PBLA with hydrophobic spacers having hydroxyl termini. These products were further conjugated with different fatty acids to form fatty acid conjugates of PEO-b-PHAA (FIG. 2). $^1$H NMR was used to measure the degree of fatty acid substitution. Attachment of a hydrophobic spacer introduces hydroxyl functional moieties to the side chains which could react with the carboxyl groups of the fatty acids. Increasing the length of the spacer group from 2 to 6 carbon atoms facilitates an increase in the degree of side chain attachment to the PHAA block. Without wishing to be bound by any particular theory, this is believed to result in a rearrangement of the hydroxyl groups away from the polymeric backbone, i.e., reduced steric hindrance, when hexyl spacers were used instead of ethyl spacers. Using the same method of synthesis, block copolymers with different structures of the core-forming block were prepared, purified, dissolved in DMF and dialyzed against water to form micellar structures. The micellar properties were determined for each structure by TEM and fluorescent probe techniques.

The data presented herein show that PEO-b-PLAAs with alkyl core structures mimic certain aspects of biological carriers for hydrophobic molecules. They self-assemble into nanoscopic, supramolecular core/shell structure where the core is rich in fatty acid esters. The shape of these micelles is spherical, except for highly substituted myristic, stearic and behenic conjugates of PEO-b-PHHA, which tend toward the formation of ellipsoids. It is believed this is due to the larger dimensions of the hydrophobic block in those constituents. Low CMC values measured for fatty acid conjugates of PEO-b-PHAA indicate a high tendency of these amphiphilic structures toward self-association in aqueous environments which tendency for self association reflects their thermodynamic stability in aqueous environments. The aliphatic core of the polymeric micelles described herein also appear rigid. Micelles with glassy cores tend to disassemble more slowly than those with a mobile core (Kataoka et al. (1993) *J. Control. Release* 24, 119). As a result, even at concentrations below the CMC, the micelles are dynamically stable and survive for a significant time in vivo.

The alkyl core of the polymeric micelles in our studies was essentially varied in four structural aspects: the length of the PLAA block, the length of the alkyl spacer, the length of the attached fatty acid and the substitution level of fatty acid on the polymeric backbone.

The substitution level of fatty acids on the polymeric backbone is the major factor affecting micellar size, shape, CMC and micropolarities. The effect of the fatty acid substitution level was investigated in PEO-b-PHCA block copolymers with two different degrees of capric acid attachment. An increase in the fatty acid content of the micellar core caused an increase in micellar size ($P<0.0001$, unpaired t test) and a decrease in CMC ($P<0.05$, unpaired t test). Average micellar size was enhanced when capric acid content of the core was increased from 7 to 44%. Increased micellar size (in the dry state) is believed to be a consequence of larger dimensions of the hydrophobic block in those structures. Owing to the hydration of the PEO surface, micellar size shows an increase in aqueous environments. However, the enhanced hydrophobicity of the core-forming block may restrict this hydration and affect the final size of the polymeric micelles in vivo. Accordingly, the results obtained from TEM measurements cannot be simply extrapolated to micellar dimensions in aqueous environments. Reduced CMC values for block copolymers with higher levels of capric acid attachment reflects the reduced free energy of micellization for those polymers. Preferential expulsion of the copolymers with larger hydrophobic segments from water (greater entropic driving force) is assumed to be the reason behind this observation. PEO-b-PHCA with 7% of capric acid attachment exhibited greater micropolarities at 500 $\mu$g/ml concentration ($I_1/I_3=1.3$). The $I_1/I_3$ in this case is even higher than values measured for benzyl core in PEO-b-PBLA at the same concentration (Lavasanifar et al. (2000) *J. Biomed. Mat. Res.* 52, 831–835). The higher $I_1/I_3$ ratios could result from high core polarities due to the expression of OH groups in the micellar core. However, incomplete localization of the pyrene probe in the micellar core could cause the same effect. This, in turn, is a result of reduced hydrophobicity in the core region when polymeric micelles with capric acid substitutions as low as 7% are used. At 7% substitution, the amount of fatty acid is not sufficient to overcome the high polarities resulting from the free hydroxyl groups present in the micellar core. Polar groups in the micellar core make the drug-loaded micelles more susceptible to dissociation and hydrolysis. Interestingly, no difference in micellar core viscosity was observed between the two species. The formation of the 1,3-(1,1'-dipyrenyl)propane excimer was considerably restricted in PEO-b-PHCA even at 7% fatty acid substitution. This result is in contrast to SDS, which shows high ratios of $I_e/I_m$ (FIG. 6).

Application of block copolymers with different lengths of the PLAA block induced changes in micellar size and core viscosity. Average micellar size was increased when length of the PHEA and PHHA was increased at the similar level of stearic acid substitution as illustrated in FIG. 3B. Increasing hydrophobic block length showed no detectable effect on CMC measured from partitioning of pyrene in micellar core (FIG. 4C). This finding seems to contradict previous observations (Kwon et al. (1993) *Langmuir* 9, 945). The presence of hydroxyl groups in the core-forming block might have hindered the effects of the block elongation in reducing CMC. Like CMC, micellar core polarity was not affected by block length, as shown in FIG. 5. Micellar core viscosity, however, was influenced by the length of the PLAA block. More rigid cores were formed when the length of PLAA was elongated from 15 to 24 (FIG. 6B). This, in turn, results in the formation of polymeric micelles with greater dynamic stability, and particle movements into or out of the core region are restricted. Collapsed conformation of the PLAA blocks in micellar core and difference in aggregation numbers are among factors causing this effect.

The length of the spacer group showed no significant effect on dialysis-prepared micellar properties. Its effect on micellar size and CMC is compared in FIGS. 3A and 4D, respectively, for PEO-b-PECA and PEO-b-PHCA having similar degrees of capric acid attachment. The difference observed in micellar size (FIG. 3B) and CMC (FIG. 4C) between PEO-b-PESA and PEO-b-PHSA is, therefore, most likely a result of an increase in the level of stearic acid substitution from 45 to 60 percent.

Except for micellar size, other properties of the system were not detectably affected when length of the fatty acid attached to the polymeric backbone was changed (Table 1), except that attachment of behenic acid (22-carbon chain) to a hexyl spacer in a high level of substitution caused an increase in core viscosity (decrease in core mobility). This unique structure lowered the formation of dipyrene probe excimer reflecting higher local viscosity in the micellar core in comparison to other polymeric micelles (Table 1). The same chemical structure with 50% of behenic acid attachment showed similar $I_e/I_m$ ratios in comparison to other structures, reflecting similar microviscosities.

Fatty acid esters of PEO-b-PHAA can be used for drug delivery as they form nanoscopic, core/shell micellar structures at very low concentrations where the core is relatively solid at room temperature. Structural modifications can be made in the core-forming block, and thus, polymeric micelles with optimized structures for the purpose of drug delivery can be designed and prepared using the teachings of the present disclosure taken with what is well known to the art. We have shown that varying the levels of fatty acid side chain and the length of the PHAA block are major factors by which the micellar structure can be tailored. Changing the level of fatty acid attachment affects micellar size, thermodynamic stability and micropolarities, whereas varying the length of the PHAA block in PEO-b-PLAA copolymers regulates micellar core viscosity, and higher core viscosities are associated with decreased dissociation rates of the loaded micelles. Increasing the core viscosity can also be achieved by conjugation of fatty acids having long chains (>22 carbon atoms) at a high level of substitution on the polymeric backbone.

Encapsulation of AmB by PEO-b-PHSA micelles was enhanced by an increase in the level of stearic acid substitution on the PHSA block (Table 3). The level of AmB encapsulated in PEO-b-PHSA micelles at 11, 50 and 70% stearic acid substitution was 0.22, 0.35 and 0.36 mol drug-:mol PEO-b-PHSA. The yield of encapsulated AmB for PEO-b-PHSA micelles was 51, 73 and 77%, respectively.

Figure 10:
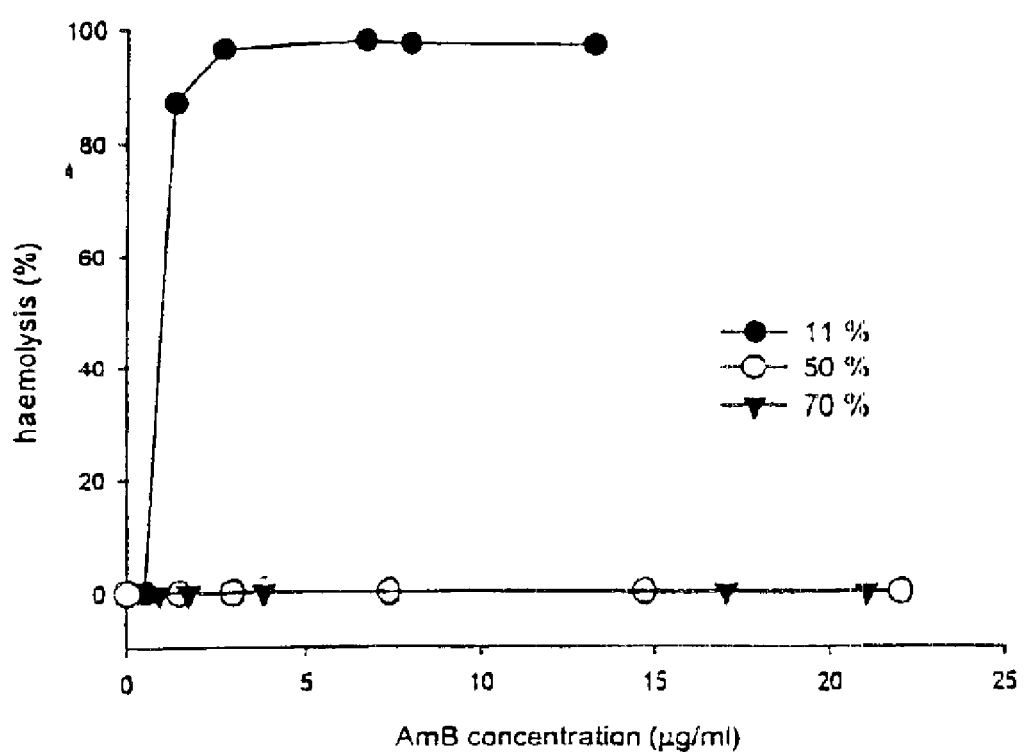
FIG. 10 shows the effect of fatty acid substitution level in PEO-b-PHSA micelles on the hemolytic activity of AmB encapsulated by solvent evaporation.

An increase in the level of stearic acid substitution in PEO-b-PHSA micelles reduced the ability of AmB to cause hemolysis (FIG. 10). At 50 and 70% stearic acid substitution AmB was completely non-hemolytic at 22 $\mu$g/ml. However, AmB at 11% stearic acid substitution was almost as hemolytic as AmB itself, causing 50% hemolysis at 1 $\mu$g/ml and 100% hemolysis at 3 $\mu$g/ml.

Figure 11:
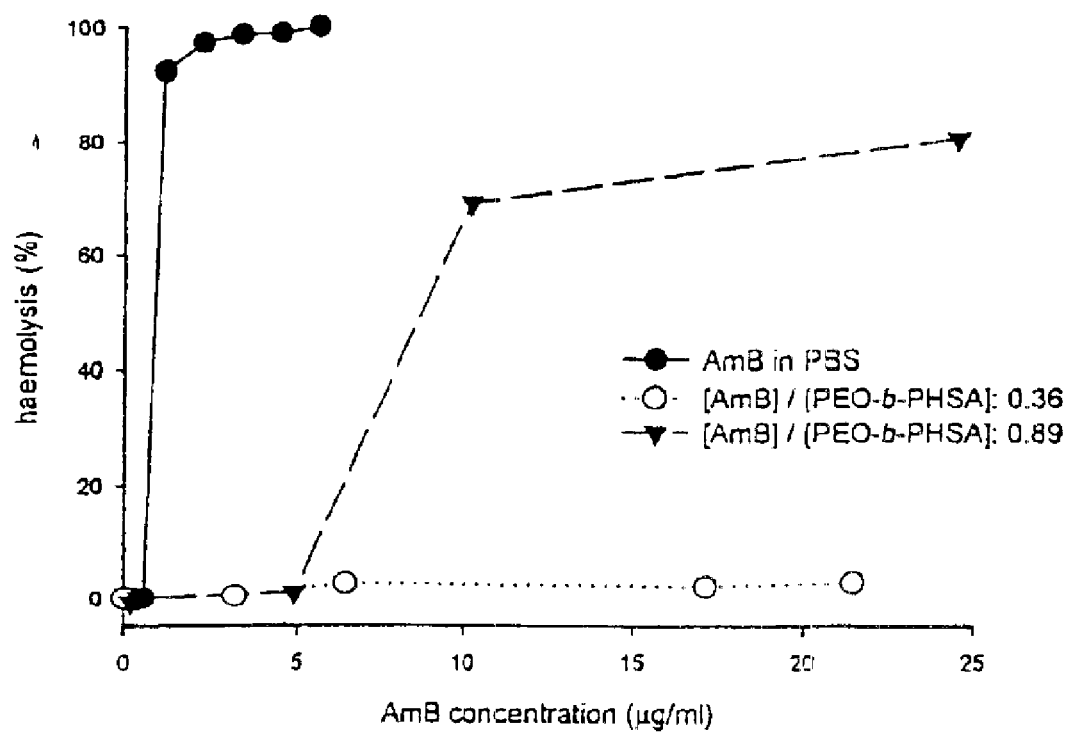
FIG. 11 shows the effect of the drug to polymer molar ratio on hemolytic activity of AmB encapsulated in PEO-b-PHSA micelles by solvent evaporation.

The effect on hemolysis was also dependent on the content of AmB in the PEO-b-PHSA micelles (FIG. 11). PEO-b-PHSA micelles at 0.36 mol drug: mol polymer were completely non-hemolytic at 22 $\mu$g/ml of AmB. On the other hand, PEO-b-PHSA micelles at 0.89 mol drug: mol polymer caused 80% hemolysis at a similar level of drug.

Figure 12A:
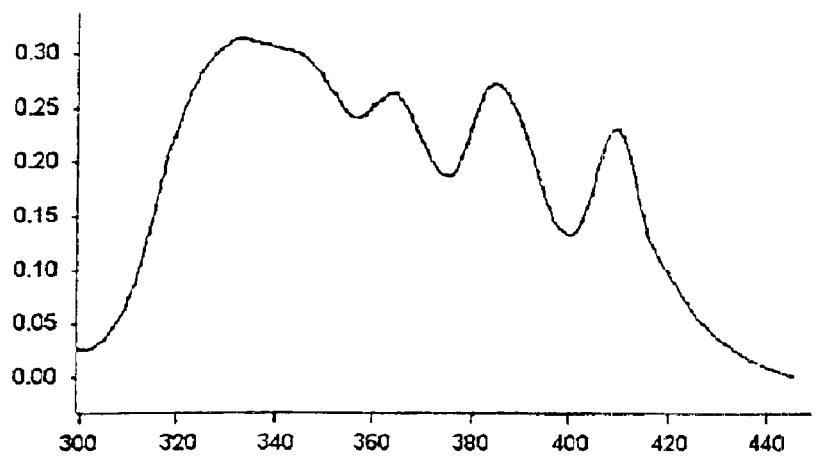
FIGS. 12A–12C illustrate absorption spectra of AmB (4 μg/ml) in PBS, pH=7.4 (FIG. 12A); PEO-b-PHSA with 11% of stearic acid substitution (FIG. 12B); and PEO-b-PHSA with 70% of stearic acid substitution (FIG. 12C).
Figure 12B:
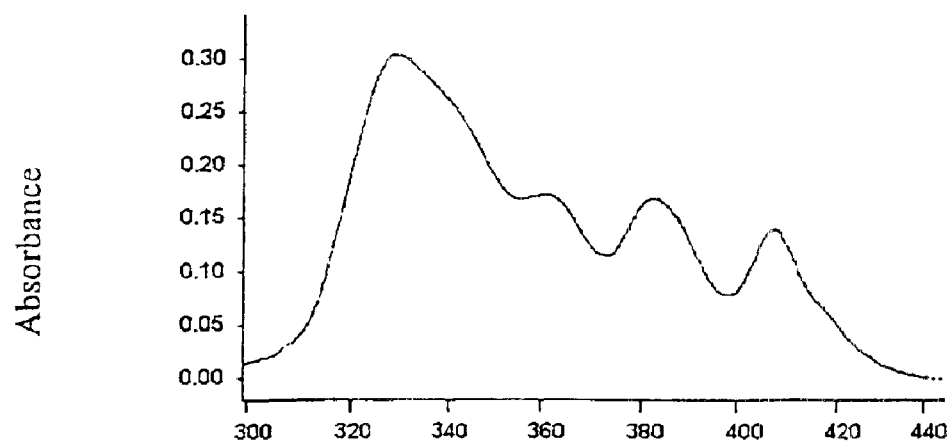
Figure 12C:
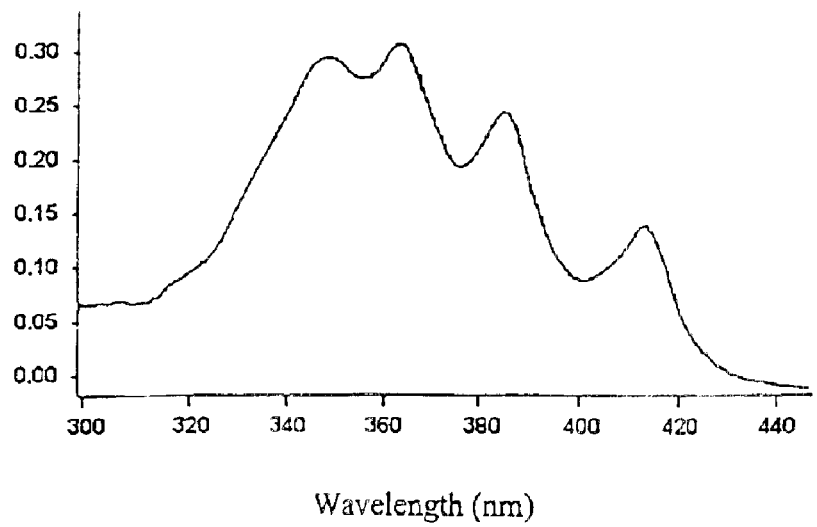
Figure 13:
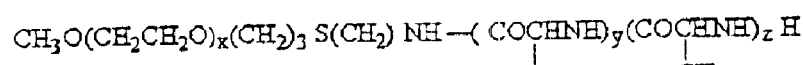
FIG. 13 shows the chemical structures of PEO-b-PHSA and AmB.
Figure 13:
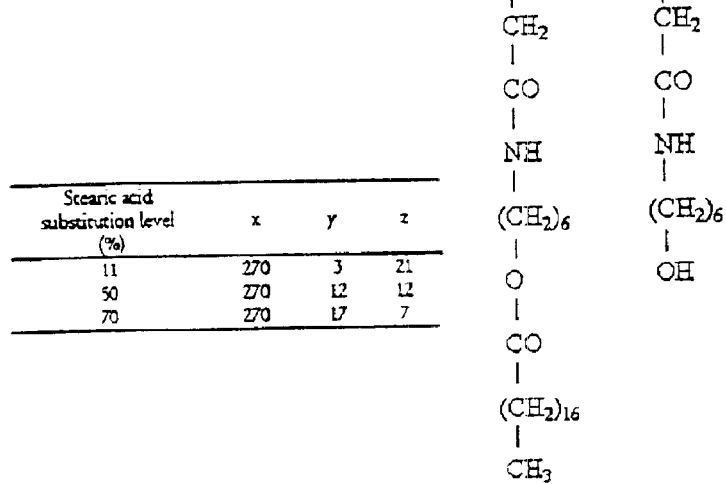
Figure 13:
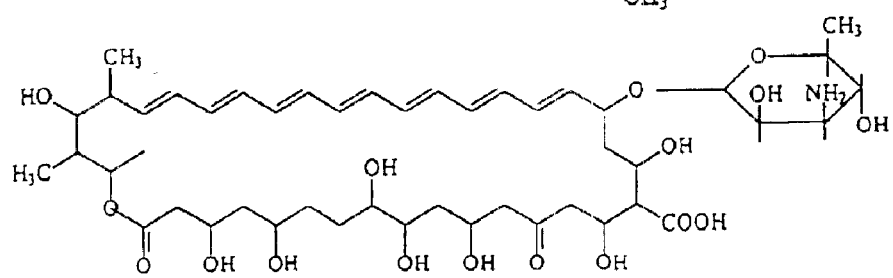

The UV/VIS spectra of encapsulated AmB in PEO-b-PHSA micelles prepared by the solvent evaporation method with 11 and 70% of stearic acid substitution and AmB itself in PBS are shown in FIG. 12. A change in the UV spectrum of AmB reflects conformational changes in AmB molecule as a result of self-association or interaction with other compounds. The UV spectrum of AmB encapsulated in PEO-b-PHSA micelles with 11% of stearic acid substitution was very similar to the UV spectrum of free AmB. At 4 µg/ml a broad absorption peak centered at 334 and three additional peaks at 364, 385 and 409 nm were observed (FIGS. 12A and 12B). The absorption peaks for AmB encapsulated in PEO-b-PHSA micelles having 70% of stearic acid substitution shifted to the red side, showing peaks at 351, 366, 387 and 415 nm (FIG. 12C). The intensity ratio at 348 nm (peak I) to that at 409 nm (peak IV) is a measure for self-aggregation state of AmB. The I/IV ratio for AmB in PBS was about 1.2 at a level of 4 µg/ml (FIG. 12A). At a similar level, for AmB encapsulated in PEO-b-PHSA micelles with 11 and 70% of stearic acid substitution, the I/IV ratio was 2.1 and 1.8, respectively (Table 3).

The antifungal activity of encapsulated AmB was compared to AmB itself by estimating MICs against the growth of three pathogenic fungi. Fungi growth was examined by an inverted microscope (×40). AmB in an isotonic solution inhibited the growth of C. albicans, C. neoformans and A. fumigatus at 0.3, 0.3 and 0.45 µg/ml, respectively (Table 4). AmB encapsulated in PEO-b-PHSA micelles was as effective as AmB itself in most of the cases. At 11 and 50% of stearic acid substitution, encapsulated AmB was even more effective than AmB itself inhibiting the growth of C. neoformans at a level of 0.18 µg/ml. (Unpaired t test, $P<0.01$). PEO-b-PHSA micelles without AmB were unable to inhibit the fungal growth at 5 mg/ml level or below.

The importance of compatibility between the core-forming block and the solubilizate has been shown in polymeric micelles (Yokoyama et al. (1998) J. Control. Release 50, 79–92; Yokoyama et al. (1998) J. Control. Release 55, 219–229; Nagarajan et al. (1986) Langmuir 2, 210–215). We explored this concept for a model aliphatic drug, AmB, and tailored the chemical structure of the core in PEO-b-PLAA micelles through attachment of aliphatic structures, i.e. fatty acids, to improve micellar properties for drug delivery. The effect of alternations in the alkyl core structure on properties of micelles formed from PEO-b-PLAA derivatives has been described herein. The effect of structural modifications namely degree of fatty acid substitution on the core-forming block on the encapsulation, hemolytic activity and anti-fungal efficacy of AmB has also been addressed herein.

The chemical structure of the core-forming block was changed in the PEO-b-PHSA block copolymers in terms of the degree of stearic acid substitution. PEO-b-PHSA block copolymers with three levels of stearic acid substitution were prepared and used to encapsulate AmB by solvent evaporation. An increase in the level of stearic acid substitution enhanced AmB encapsulation (Table 3) while reducing its membrane activity toward red blood cells (FIG. 10). Under identical loading conditions, the yield of AmB encapsulation was 51, 72 and 77% for polymers with 11, 50 and 70% of stearic acid substitution, respectively (Table 3). AmB in 11% substituted polymer caused 100% hemolysis at 3 µg/ml but it was non-hemolytic at 22 µg/ml after encapsulation in PEO-b-PHSA micelles with 50 and 70% of stearic acid substitution (FIG. 10). The extinction of hemolytic activity of AmB obtained by encapsulation in PEO-b-PHSA micelles was acquired at a drug content of 0.4 mol AmB: mol PEO-b-PHSA but was not as much at a 0.9 mol drug: mol polymer ratio (FIG. 11).

FIG. 7 shows that AmB loaded in micelles prepared by the solvent evaporation method are significantly reduced in hemolytic activity as compared with micelles loaded by dialysis. The hemolytic activity of AmB in an uncomplexed form is also shown.

Figure 8A:
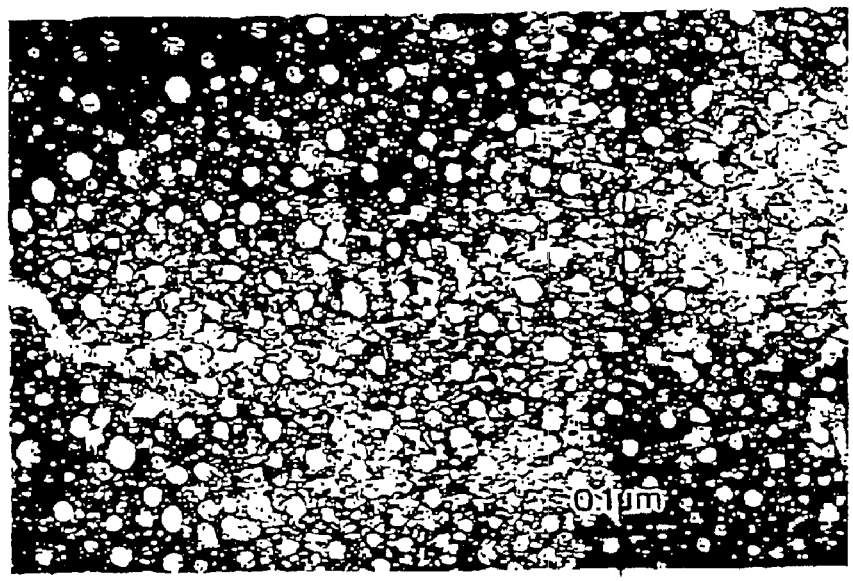
FIGS. 8A–8B provide TEM images of PEO-b-PHSA micelles prepared by the solvent evaporation method (prior to freeze-drying) (FIG. 8A) and the dialysis method (FIG. 8B) (magnification of 18,000×6).
Figure 8B:
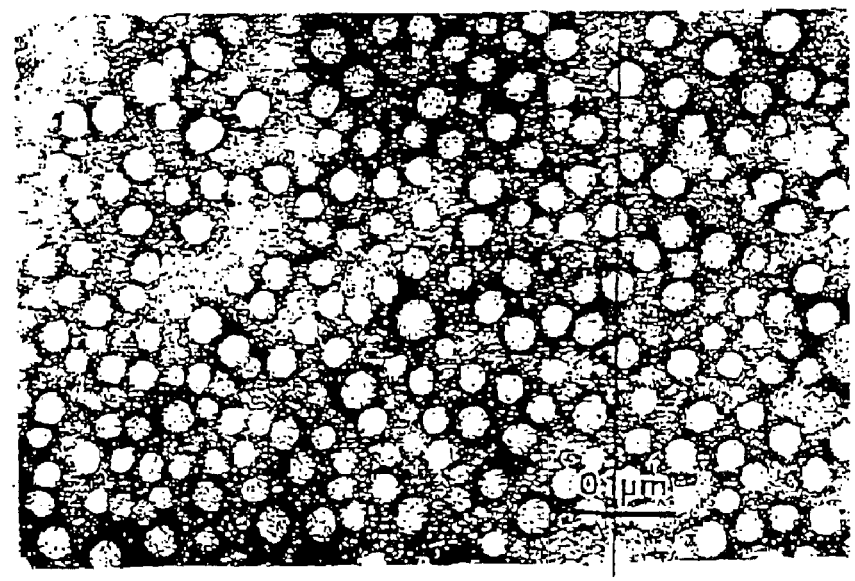

FIGS. 8A and 8B compared AmB-loaded micelles prepared by the solvent evaporation and dialysis methods, respectively. The solvent evaporation method is shown in FIG. 9.

Despite reduced toxicity toward human red blood cells, encapsulated AmB in PEO-b-PHSA micelles remained active against pathogenic fungi in vitro. The antifungal activity of AmB was not affected by the level of stearic acid substitution in the micellar carrier (Table 4).

AmB binds to serum lipoproteins, which have cores rich in triglycerides, and interacts with lipid bilayer membranes (Brajtburg and Bolard (1996) Clin. Microbiol. 9, 512–531). The conformational change in AmB molecule as a result of this interaction causes a bathochromic shift in the position of peak IV from 409 nm (for monomeric AmB) to 414 nm (for AmB complex) in its UV/VIS spectrum (Barwicz et al. (1991) Biochem. Biophys. Res. Comm. 181–722–728). We observed a similar shift in the UV/VIS spectra of AmB in PEO-b-PHSA micelles with higher levels of stearic acid substitution (FIGS. 12A and 12C). Therefore, a preferential encapsulation of AmB in PEO-b-PHSA micelles with more fatty acid esters in the core appears to be caused by a favorable interaction between the drug and the lipid core. The same reason might have caused a sustained drug release from micellar systems with high levels of fatty acid esters in the core leading to AmB delivery in a monomeric state. Monomeric AmB is non-toxic towards mammalian cells but active against fungal cells. In contrast, AmB encapsulated in PEO-b-PHSA micelles with 11% of stearic acid substitution absorbs UV light at similar wavelength as AmB itself (409 nm) reflecting lack of interaction (FIG. 12B). In comparison to AmB itself, a higher I/IV ratio of AmB in PEO-b-PHSA micelles with low levels of stearic acid substitution, instead, indicates the presence of encapsulated AmB aggregates (Table 3). A rapid or aggregated AmB release might be the cause of AmB toxicity towards red blood cells in micelles with lower levels of fatty acid substitution or higher drug content.

The level of stearic acid substitution in PEO-b-PHSA can be adjusted to enhance encapsulation and efficacy of AmB as a result of enhanced interaction with the micellar core. The attenuated in vitro toxicity of AmB in PEO-b-PHSA micelles with higher levels of stearic acid substitution reflects a crucial role for controlling the rate of AmB release. Thus, PEO-b-PHSA micelles with higher levels of fatty acid esters in the core act as a nanoscopic depots with long circulating properties for AmB delivery. The efficacy of AmB is improved for long-circulating liposomal AmB in a murine model of candidiasis (Van Etten et al. (1998) Antimicrob. Agent. Chemother. 42, 2431–2433). The long circulating system also reduces the dose, the risk of long-term toxicities and the cost of AmB therapy associated with the administration of standard lipid formulations of AmB.

In sum, chemical tailoring of the core in PEO-b-PLAA micelles via increasing the presence of compatible moieties, i.e. fatty acid esters, leads to a better encapsulation and reduced hemolytic activity for AmB. As a result, the polymeric micellar formulation of the present invention, which is made by solvent evaporation technology, provides effective solubility, reduced hemolytic activity and good antifungal efficacy for AmB in vitro and in vivo. PEO-b-PHSA self assembles into micelles that encapsulate AmB by a solvent evaporation method, the overall concentration of AmB in water is clinically relevant for use in humans and animals for systemic fungal diseases, and the toxicity of the AmB in terms of hemolysis is dramatically decreased over prior art formulations.

The encapsulated AmB-containing compositions of the present invention are improved with respect to toxicity and with respect to release properties. It has been demonstrated that the present compositions are effective in inhibiting the growth of representative fungal pathogens in vitro. These compositions are similarly effective in vivo after administration by a parenteral route, desirably by intravenous injection, and especially by intravenous perfusion. Pathogenic fungi against which the AmB of the present invention is effective include, without limitation, species of Histoplasma, Cryptococcus, Candida, Aspergillus, Blastomyces, Mucor, Torulopsis, Rhizopus, Absidia, and causative agents of coccidiodomycosis and paracoccidioidomycosis, among others. Anticancer agents such as taxol and the antineoplastic derivatives of taxol are also reduced in toxicity when encapsulated in micelles according to the present invention and delivered by parenteral administration, for example by intravenous injection or infusion. It is preferred that the drug-loaded micelles of the present invention are freeze-dried after preparation and stored in the dry state in a manner consistent with maintenance of the activity of the drug, as known in the art for a particular drug. The dry micelles are reconstituted in a pharmaceutically acceptable carrier such as sterile physiological saline or a sterile dextrose solution, e.g., 5% dextrose, and after thorough hydration, they can be filtered (optionally through a 0.22 μm filter) prior to administration. The micelles of the present invention are administered at a similar dosage as is Amphotericin B in prior art liposomal forms.

All references cited in the present application are incorporated by reference herein to the extent that there is no inconsistency with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Synthesis of Fatty Acid Esters of PEO-block-poly (hydroxy-alkyl L-aspartamide)

The synthesis of PEO-b-PBLA block copolymers is described in detail elsewhere (Yokoyama et al. (1992) Bioconj. Chem. 3, 295). PEO-b-PBLA block copolymers were synthesized by ring-opening polymerization of b-benzyl L-aspartate N-carboxyanhydride using α-methoxy-ω-amino-PEO as an initiator ($M_n$=12,000 gmole$^{-1}$, $M_w/M_n$=1.05, amine functionality=0.96). Based on $^1$H NMR spectroscopy, the degree of polymerization of the PBLA block in the samples was either 15 or 24. To differentiate between these samples, a nomenclature of 12-15 or 12-24 is defined in this paper based on molecular weight of the PEO block (12000 gmole$^{-1}$) and the degree of polymerization of the PLAA block (15 or 24).

PEO-b-PBLA (0.10 mmol BLA units) was dissolved in dried N,N-dimethylformamide (DMF) (5 mL) with the aid of stirring and slight heating. Subsequently, 2-aminoethanol or 6-aminohexanol (10 eq) and 2-HP (0.3 mmol) were added. The reaction mixture was stirred for 24 h at 25° C. and poured into vigorously stirred cold isopropanol (50 mL). The white precipitate was washed with isopropanol and diethyl ether and dried under vacuum. The complete removal of benzyl groups was evidenced by $^1$H NMR in chloroform-d (AM-300 MHz) and by absorption spectroscopy (Milton-Roy 3000).

In the second step, PEO-b-poly(hydroxyalkyl L-aspartamide) (PEO-b-PHAA) (12–15) was esterified with either hexanoic (C=6), capric (C=10), myristic (C=14), stearic (C=18) or behenic acid (C=22). Fatty acid (5 eq), DCC (0.070 mmol) and DMAP (0.010 mmol) were added to a solution of PEO-b-PHAA (0.003 mmol HAA units) in dried dichloromethane (5.0 mL). The mixture was stirred at room temperature for 24 h. The product was precipitated in cold isopropanol (50 mL), washed with either isopropanol or diethyl ether, collected by centrifugation and dried under vacuum. The same method of preparation was used to attach stearic acid to PEO-b-PHAA (12–24). The products were characterized by $^1$H NMR in chloroform-d (AM-300 MHz).

Unless otherwise noted, PEO-b-PHSA was prepared from PEO-block-poly(_-benzyl L-aspartate) (PEO-b-PBLA) as described previously (Lavasanifar et al. (2000) J. Biomed. Mater. Res. 52 (2000) 831–835). The molecular weight of PEO and the number of BLA units in PEO-b-PBLA were 12,000 g mol$^{-1}$ ($M_w/M_n$=1.05) and 24, respectively. Briefly, PEO-b-PBLA was reacted with 6-aminohexanol at 25° C. in the presence of 2-hydroxypyridine as a catalyst. PEO-block-poly(hydroxyhexyl L-aspartamide) (PEO-b-PHHA) was formed, providing hydroxyl groups in the side chains. Stearic acid was then reacted with PEO-b-PHHA in dry dichloromethane with the aid of dicyclohexylcarbodiimide and dimethylaminopyridine. The reaction time was varied between 2 and 72 hr to achieve varied levels of stearic acid substitution on the PHHA block. The degree of fatty acid substitution (mol stearic acid: mol reacted and unreacted hydroxyl groups) was estimated by $^1$H-NMR in chloroform-d (AM-300 MHz).

Example 2

Micelle Formation From Fatty Acid Esters of PEO-b-PHAA

In experiments carried out to compare fatty acid aliphatic chain length, the dialysis method was used to prepare micelles. Micellization of polymers was achieved by dissolving 15 mg of each polymer in 4.0 ml of DMF with the aid of slight heat. Doubly distilled water was then added to this solution in a drop-wise manner (one drop per 20 s) until the final water concentration was 10–15% (v/v). A dialysis membrane with a molecular cutoff of 12,000–14,000 gmole$^{-1}$ was used to replace the organic solvent with distilled water overnight at room temperature replacing the medium three times. Micelles were then passed through 0.22 μM filters.

In certain other experiments, the dialysis method as described in Lavasanifar et al. (2000) supra was used. AmB (400 mg) and PEO-b-PHSA (20 mg) were both dissolved in 1.2 ml of N,N-dimethylsulfoxide. Distilled water was added to the solution in a drop-wise manner (1 drop/20 sec) until the water content reached 80% v/v. The solution of AmB and PEO-b-PHSA was dialysed against distilled water overnight, filtered (0.22 μm) and freeze-dried.

The solvent evaporation method for the preparation of AmB-encapsulated micelles is as follows. AmB (470 μg or 2 mg) and PEO-b-PHSA (20 mg) were dissolved in methanol (5.0 ml or 10 ml) in a round bottom flask. Methanol was evaporated under vacuum at 300 mm Hg at 40° C. in 15 min. Alternatively, the solvent evaporation can be accomplished at room temperature at a pressure of about 100 mm Hg or at about 33° C. and about 200 mm Hg. Distilled water was added to the polymer/drug film, the solution was incubated at 40° C. for 10 min and vortexed for 30 seconds afterwards. The micellar solution was filtered (0.22 μm) and freeze-dried.

The freeze-dried samples of AmB in PEO-b-PHSA micelles were reconstituted in water and filtered (0.22 μm). An aliquot of the solution in water was diluted with an equal volume of N,N-dimethylformamide (DMF), and the drug content measured from the UV/VIS absorbance of AmB at 412 nm (Pharmacia Biotech Ultraspec 3000).

As an alternative to the solvent evaporation technique described herein for the incorporation of a polyene antibiotic into amphiphilic polymer micelles, one can also produce micelles having properties about the same as those prepared by solvent evaporation as described herein by rapidly jetting in the polyene antibiotic (or other compound of interest) into warm water containing the amphiphilic polymeric material dissolved in a solvent such as methanol or chloroform, with rapid mixing, and subsequent recovery of the drug-loaded micelles. The micelles can then be freeze dried as described herein.

Example 3

Transmission Electron Microscopy (TEM)

Samples for TEM were prepared by placing 20 μl of polymeric micellar solution (1.0–1.5 mg/ml) on a copper-coated grid. A portion (20 μl) of 2% phosphotungstic acid in water was added as the negative stain. After 1 min excess fluid was removed using filter paper, and images were obtained at a magnification of 18,000 times (75 kV) (Hitachi H 7000). Apparent micellar diameters were measured, and a mean diameter +SD was calculated based on at least 120 measurements.

Example 4

Size Exclusion Chromatography (SEC)

AmB was dissolved in 0.10 M phosphate buffer, pH 7.4, with the aid of N,N-dimethylsulfoxide (DMSO) to provide concentrations from 1.0 to 100 μg/ml. The amount of DMSO in the final product was <1% (v/v). Freeze-dried PEO-b-PHSA micelles with or without AmB were dissolved in a 0.10 M phosphate buffer to provide a level of 0.5 mg/ml for polymer. Samples of 125 μl were injected into a Hydrogel 2000 (Waters) column after it was equilibrated with phosphate buffer 0.10 M (pH=7.4) at a flow rate of 0.8 ml/min (Waters B 15 LC system). Eluted material was detected using a UV/VIS detector (Waters 486) set at 210 and 410 nm for PEO-b-PHSA and AmB, respectively. The column was calibrated with dextran standards ($8.05H10^5$ $B9.11H10^6$ g $mol^{-1}$) using refractive index detection (Precision Detectors 2000).

Example 5

UV/VIS Spectroscopy

Freeze-dried samples of AmB in PEO-b-PHSA micelles with 11 and 70% stearate substitution were dissolved in PBS, pH=7.4, at 4 μg/ml of AmB. DMSO was used to solubilize AmB in PBS, pH=7.4, at a similar concentration. The level of DMSO in the final sample was <1% (v/v). The UV/VIS spectra of AmB in different samples were recorded from 300 nm to 450 nm.

Example 6

Hemolytic Activity of AmB Toward Human Red Blood Cells

Human blood was collected and centrifuged (2000 rpm). The supernatant and buffy coat were pipetted off and the red blood cells (RBCs) were diluted with an isotonic phosphate buffer, pH 7.4. The proper dilution factor was estimated from the UV/VIS absorbance of hemoglobin at 576 nm in the supernatant after RBCs were lysed by 20 μg/ml of AmB. A properly diluted sample of RBCs gives an absorbance of 0.4–0.5. Solutions of diluted RBCs (2.5 ml) with varied levels of AmB in different samples were incubated at 37° C. for 30 min. Samples were then placed in ice to stop hemolysis. The unlysed RBCs were removed by centrifugation at 14,000 rpm (about 7000×g) for 20 sec. The supernatant was collected and analyzed for hemoglobin by UV/VIS spectroscopy at 576 nm. The percent of hemolyzed RBCs was determined using this equation: % hemolysis= $100(Abs-Abs_o)/(Abs_{100}-Abs_o)$, where Abs, $Abs_o$ and $Abs_{100}$ are the absorbance for the sample, control with no AmB and control in the presence of 20 μg/ml AmB, respectively.

Example 7

Minimal Inhibitory Concentration (MIC) of AmB

AmB in PEO-b-PHSA micelles was dissolved in isotonic sodium chloride solution giving an AmB level of 200 μg/ml. AmB was dissolved in DMSO and diluted further with the isotonic sodium chloride solution to give the same concentration. The level of DMSO in the final solution was <1% v/v. Samples of PEO-b-PHSA micelles in sodium chloride solution were also used as controls. Solutions of 20 μl from these samples were diluted with the culture medium (RPMI 1640) (80 μl) in the first microwell. The next 11 microwells had serial two-fold diluted solutions. To each microwell, 100 μl of the inoculum containing $5×10^3$ CFU/ml of fungal pathogen (Candida albicans, Aspergillus fumigatus or Cryptococcus neoformans) in culture medium was added, giving a total volume of 200 μl per well. Microwell containers were incubated at 35° C. for 24 hr. Organism and medium controls were performed simultaneously to check the growth of organisms and sterility of culture medium, respectively. The MIC was defined as the minimum concentration of AmB that shows a full inhibition of fungal growth in the well, when examined using an inverted microscope (H40). All tests were repeated three times.

Example 8

Estimation of the Critical Micelle Concentration and Micellar Core Polarity by Fluorescent Probe Techniques By following changes in the fluorescence excitation and emission spectra of pyrene in the presence of varied concentrations of block copolymers, the critical micelle concentration (CMC) and the polarity of the micellar core for each block copolymer were determined, respectively. Pyrene was dissolved in acetone and added in a known amount to 5 ml volumetric flasks to provide a concentration of 6 H $10^{-7}$ M in the final solutions. Acetone was then removed and replaced with aqueous polymeric micellar solutions (5 ml) with concentrations ranging from 0.5 to 1000 µg/ml. Samples were heated at 65EC for an hour, cooled to room temperature overnight and deoxygenated with nitrogen gas prior to fluorescence measurements. The excitation and emission spectrum of pyrene for each sample was then obtained using Fluoromax DM-3000 fluorescence spectrometer at room temperature. For fluorescence emission spectra, the excitation wavelength was chosen at 339 nm and for excitation spectra, the emission wavelength was set at 390 nm. Spectra were accumulated with an excitation and emission bandwidth of 4.25 nm. The intensity ratio of peaks at 339 nm to those at 334 nm from the excitation spectrum were plotted against the logarithm of copolymer concentration to measure the CMC. A plot of the intensity ratio of first to the third band from the emission spectrum of pyrene vs. logarithm of copolymer concentration was used to estimate micelle core polarity.

Example 9

Estimation of Core Viscosity by Fluorescent Probe Measurements

The viscosity of the micelle cores above the CMC was estimated with fluorescent probe techniques by measuring excimer to monomer intensity ratio ($I_e/I_m$) of 1,3-(1,1=-dipyrenyl)propane at 376 and 480 n, respectively. 1,3-(1,1=-dipyrenyl)propane was dissolved in a known volume of chloroform to give a final concentration of 2H $10^{-7}$ M. Chloroform was then evaporated and replaced with 5 ml of aqueous solutions of polymeric micelles with a concentration of 500 µg/ml or sodium lauryl sulfate at 5 mg/ml. Samples were heated at 65EC for an hour and cooled to room temperature overnight. A stream of nitrogen gas was used to deoxygenate samples prior to fluorescence measurements. Emission spectrum of 1,3-(1,1=-dipyrenyl)propane was obtained at room temperature using an excitation wavelength of 333 nm. Excitation bandwidth and integration times were set at the same values as the previous experiment.

Example 10

Statistical Analysis

Data obtained from CMC, micellar size, polarity and viscosity measurements were analyzed by Statistical Analysis Software (SAS) using either ANOVA, Duncan=s test or unpaired t test.

Example 11

Materials

Dicyclocarbodiimide (DCC), dimethylaminopyridine (DMAP), 6-aminohexanol, fatty acids and pyrene were purchased from Sigma Chemical Co., St. Louis, Mo. 2-hydroxypyridine (2-HP) and 2-aminoethanol were purchased from ICN. 1,3-(1,1=-dipyrenyl)propane was purchased from Molecular Probes, Eugene, Oreg. All other chemicals were reagent grade. PEO-block-poly(hydroxyalkyl L-aspartamide) block copolymers were obtained from K. Kataoka; they are described in U.S. Pat. No. 5,449,513; see also a description of the synthesis of PEO-b-PBLA block copolymers in Yokoyama et al. (1992) Bioconj. Chem. 3, 295.

TABLE 1

The effect of fatty acid chain length on micellar properties in PEO-b-PHAA polymer block length (12–15).

| Spacer group | Fatty acid chain length (#C) | Substitution level (%) | Size ± SD (nm) | CMC ± SD (mg/mL) | $I_1/I_3$ ± SD | $I_e/I_m$ ± SD |
|---|---|---|---|---|---|---|
| ethyl | 6 | 44 | 16.4 ± 3.2 | 39 ± 5 | 1.05 ± 0.01 | 0.16 ± 0.01 |
| ethyl | 10 | 43 | 17.6 ± 3.3 | 32 ± 2 | 1.00 ± 0.02 | 0.15 ± 0.02 |
| ethyl | 14 | 42 | 17.7 ± 3.9 | 34 ± 16 | 1.03 ± 0.02 | 0.15 ± 0.01 |
| ethyl | 18 | 47 | 18.0 ± 5.9 | 39 ± 7 | 1.06 ± 0.03 | 0.15 ± 0.05 |
| hexyl | 10 | 57 | 18.1 ± 3.3 | 26 ± 3 | 1.01 ± 0.03 | 0.12 ± 0.01 |
| hexyl | 14 | 65 | 21.3 ± 5.9 | 14 ± 6 | 1.02 ± 0.01 | 0.12 ± 0.01 |
| hexyl | 18 | 60 | 21.6 ± 3.4 | 23 ± 5 | 1.02 ± 0.01 | 0.15 ± 0.04 |
| hexyl | 22 | 65 | 21.8 ± 7.4 | 9 ± 2 | 1.08 ± 0.01 | 0.08 ± 0.01 |
| hexyl | 22 | 48 | NA | 27 ± 4 | 1.03 ± 0.01 | 0.12 ± 0.01 |

TABLE 2

The effect of loading process on encapsulation of AmB by PEO-b- PHSA micelles.

| Loading method | PEO-b-PHSA (mg) | Initial level of AmB (mg) | Loaded AmB (mg) | AmB: PEO-b-PHSA (mol:mol) | Yield (%) | Elution time (min) |
|---|---|---|---|---|---|---|
| Dialysis | 20 | 406 | 244 | 0.25 | 60 | 10.8 |
| Solvent evaporation | 20 | 470 | 340 | 0.35 | 73 | 10.6 |

TABLE 3

The effect of fatty acid substitution of the core-forming block on the ecapsulation of AmB by PEO-b-PHSA micelles by solvent evaporation.

| Stearic acid substitution level (%) | PEO-b-PHSA (mg) | Initial level of AmB (mg) | AmB (mg) | AmB: PEO-b-PHSA (mol:mol) | Yield (%) | I/IV ratio |
|---|---|---|---|---|---|---|
| 11 | 20 | 470 | 240 | 0.22 | 51 | 2.2 |
| 50[b] | 20 | 470 | 340 | 0.35 | 73 | Nd |
| 70[c] | 20 | 470 | 360 | 0.36 | 77 | 1.8 |
| 50 | 20 | 1870 | 992 | 0.89 | 53 | |

TABLE 4

The effect of fatty acid substitution of the core-forming block on the in vitro antifungal activity of AmB encapsulated by PEO-b-PHSA micelles in comparison to AmB alone.

| AmB in: | Loading method | MIC " SD (mg/ml) | | |
|---|---|---|---|---|
| | | C. albicans | C. neoformans | A. fumigatus |
| Saline | — | 0.30 ± 0.00 | 0.30 ± 0.00 | 0.45 ± 0.00 |
| PEO-b-PHSA 11% | Solvent evaporation | 0.35 ± 0.09 | 0.18 ± 0.04 | 0.60 ± 0.00 |

TABLE 4-continued

The effect of fatty acid substitution of the core-forming block on the in vitro antifungal activity of AmB encapsulated by PEO-b-PHSA micelles in comparison to AmB alone.

| AmB in: | Loading method | MIC " SD (mg/ml) | | |
|---|---|---|---|---|
| | | C. albicans | C. neoformans | A. fumigatus |
| PEO-b-PHSA 50% | Solvent evaporation | 0.27 ± 0.04 | 0.18 ± 0.05 | 0.60 ± 0.00 |
| PEO-b-PHSA 70% | Solvent evaporation | 0.33 ± 0.11 | 0.23 ± 0.07 | 0.35 ± 0.09 |
| PEO-b-PHSA 50% | Dialysis | 0.71 ± 0.19 | 0.25 ± 0.09 | 0.82 ± 0.38 |

What is claimed is:

1. A method for reducing the toxicity of a therapeutic agent which is polyene antibiotic, an acylated prodrug, an acylated cis-platin, paclitaxel or tamoxifen., said method comprising the steps of:
   (a) dissolving a therapeutic agent which is a polyene antibiotic, paclitaxel, tamoxifen, acylated prodrug, or an acylated cis-platin and polyethylene oxide-block-poly-N-(alkyl-fatty acyl) L-aspartamide (polymer) in a solvent, said polymer having a number of L-aspartate monomer residues from 10 to 30, said alkyl having from 2 to 8 carbon atoms and said fatty acyl having from 8 to 28 carbon atoms, in a solvent to produce a solution;
   (b) evaporating the solvent from the solution of step (a) under conditions selected from the group consisting of 40° C. and 300 mm mercury, 33° C. and 200 mm mercury and 26° C. and 100 mm mercury to produce a therapeutic agent-polymer film;
   (c) adding water to the therapeutic agent-polymer film of step (b) and mixing vigorously,
whereby micelles comprising a therapeutic agent and polymer are formed.

2. The method of claim 1 wherein the solvent is methanol, wherein the polyene antibiotic is Amphotericin B (AmB), wherein the number of L-aspartate monomer residues is from 14 to 26, and wherein the fatty acyl is from 12 to 20 carbon atoms and wherein the acyl is 6 carbon atoms.

3. The method of claim 2 wherein the fatty acyl is from 12 to 22 carbon atoms.

4. The method of claim 3 wherein the fatty acyl group is 18 carbon atoms (stearate).

5. The method of claim 2 wherein the conditions for evaporating the solvent are 40° C. and 300 mm mercury.

6. The method of claim 4 wherein stearate is present in the polymer at a level of substitution from 35% to 70%.

7. The method of claim 6 wherein stearate is present in the polymer at a level of substitution of 50%.

8. The method of claim 6 wherein stearate is present in the polymer at a level of substitution of about 70%.

9. The method of claim 6 wherein the polymer comprises a PEO component having a molecular weight of 10,000 to 14,000.

10. The method of claim 9 wherein the polymer comprises a PEO component having a molecular weight of about 12,000.

11. The method of claim 1 further comprising the step of freeze-drying the micelles formed in step (c).

12. The method of claim 1 further comprising the step of adding mannitol, dextrose, sucrose or trehalose.

13. A composition comprising micelles comprising a therapeutic agent selected from the group consisting of a polyene antibiotic, an acylated prodrug, an acylated cis-platin paclitaxel or tamoxifen, and polyethylene oxide-block-poly(N(6-hexyl stearate) L-aspartamide (PEO-b-PHSA), said PEO-b-PHSA having a number of L-aspartate monomer residues from 10 to 30.

14. The composition of claim 13 wherein said polyene antibiotic is Amphotericin B.

15. The composition of claim 13 wherein further comprising a pharmaceutically acceptable carrier.

16. The composition of claim 13 further comprising mannitol, dextrose, sucrose or trehalose.

17. The composition of claim 15 wherein the pharmaceutically acceptable carrier is a sterile aqueous solution comprising trehalose, mannitol, dextrose, sucrose or sodium chloride.

* * * * *

UNITED STATES PATENT AND TRADEMARK OFFICE
CERTIFICATE OF CORRECTION

PATENT NO. : 6,939,561 B2
APPLICATION NO. : 10/187317
DATED : September 6, 2005
INVENTOR(S) : Glen S. Kwon et al.

It is certified that error appears in the above-identified patent and that said Letters Patent is hereby corrected as shown below:

At column 5, line 15, replace "2.9±106" with --$2.9 \times 10^6$--.
At column 11, line 44, replace "alternations" with --alterations--.
At column 15, Example 4, line 59, replace "($8.05H10^5$ $B9.11H10^6$ g mol$^{-1}$)" with --($8.05 \times 10^5 – 9.11 \times 10^6$ g mol$^{-1}$)--.

At column 17
Line 1, replace "6 H $10^{-7}$" with --$6 \times 10^{-7}$--.
Line 4, replace "65EC" with --65°C--.
Line 30, replace "2H $10^{-7}$" with --$2 \times 10^{-7}$--.
Line 35, replace "65EC" with --65°C--.

Signed and Sealed this

Nineteenth Day of February, 2008

JON W. DUDAS
*Director of the United States Patent and Trademark Office*